(12) United States Patent
Fabian, Jr.

(10) Patent No.: US 8,062,373 B2
(45) Date of Patent: Nov. 22, 2011

(54) SPINE SURGERY METHOD AND MOTION PRESERVING IMPLANT

(76) Inventor: Henry F. Fabian, Jr., Steamboat Springs, CO (US)

( * ) Notice: Subject to any disclaimer, the term of this patent is extended or adjusted under 35 U.S.C. 154(b) by 777 days.

(21) Appl. No.: 12/164,612

(22) Filed: Jun. 30, 2008

(65) Prior Publication Data

US 2009/0048676 A1 Feb. 19, 2009

Related U.S. Application Data

(63) Continuation-in-part of application No. 11/236,068, filed on Sep. 27, 2005.

(51) Int. Cl.
*A61F 2/44* (2006.01)
(52) U.S. Cl. .................. 623/17.16; 623/17.11
(58) Field of Classification Search ............... 623/17.11, 623/13, 15, 16
See application file for complete search history.

(56) References Cited

U.S. PATENT DOCUMENTS

| | | |
|---|---|---|
| 3,867,728 A | 2/1975 | Stubstad et al. |
| 4,309,777 A | 1/1982 | Patil |
| 4,401,112 A | 8/1983 | Rezaian |
| 4,553,273 A | 11/1985 | Wu |
| 4,643,178 A | 2/1987 | Nastari et al. |
| 4,759,769 A | 7/1988 | Hedman et al. |
| 4,772,287 A | 9/1988 | Ray et al. |
| 4,820,305 A | 4/1989 | Harms et al. |
| 4,863,477 A | 9/1989 | Monson |
| 4,932,969 A | 6/1990 | Frey et al. |
| 4,932,975 A | 6/1990 | Main et al. |
| 4,946,378 A | 8/1990 | Hirayama et al. |
| 5,002,576 A | 3/1991 | Fuhrmann et al. |
| 5,071,437 A | 12/1991 | Steffee |
| 5,123,926 A | 6/1992 | Pisharodi |
| 5,156,839 A | 10/1992 | Pennell et al. |
| 5,246,458 A | 9/1993 | Graham |
| 5,314,477 A | 5/1994 | Marnay |
| 5,439,464 A | 8/1995 | Shapiro |
| 5,505,732 A | 4/1996 | Michelson |
| 5,571,192 A | 11/1996 | Schonhoffer |
| 5,772,661 A | 6/1998 | Michelson |
| 5,782,919 A | 7/1998 | Zdeblick et al. |
| 5,785,647 A | 7/1998 | Tompkins et al. |
| 5,976,187 A | 11/1999 | Richelsoph |

(Continued)

OTHER PUBLICATIONS

Disc Orthopaedic Technologies to Introduce B-Twin Expandable Spinal Fusion System at NASS, by N.J. Monroe, dated Sep. 26th (no year given), article from PRNewswire, copyright 1996-2006 PR Newswire Association LLC, webpage (http://www.prnewswire.com/cgi-bin/stories.pl?ACCT=104&STORY=/www/story//09-26-2005/0004131865&EDATE=), USA.

(Continued)

*Primary Examiner* — Thomas C. Barrett
*Assistant Examiner* — Christine Nelson
(74) *Attorney, Agent, or Firm* — Timothy D. Bennett; Emerson Thomson Bennett

(57) ABSTRACT

A spinal implant may be deployable, when positioned within a vertebral space between a pair of vertebral bodies, from a first laterally non-expanded condition to a second laterally expanded condition. The spinal implant may include top beams and bottom beams separated by at least one post that is, in one embodiment, length variable in response to a load put on the implant after deployment of the implant. In an alternate embodiment, at least one post is laterally variable in response to a load put on the implant. In another embodiment, one of the posts may be centrally located.

29 Claims, 33 Drawing Sheets

U.S. PATENT DOCUMENTS

| | | | |
|---|---|---|---|
| 6,080,155 | A | 6/2000 | Michelson |
| 6,093,205 | A | 7/2000 | McLeod et al. |
| 6,193,757 | B1 | 2/2001 | Foley et al. |
| 6,200,348 | B1 | 3/2001 | Biedermann et al. |
| 6,206,922 | B1 | 3/2001 | Zdeblick et al. |
| 6,228,022 | B1 | 5/2001 | Friesem et al. |
| 6,283,966 | B1 | 9/2001 | Houfburg |
| 6,395,031 | B1 | 5/2002 | Foley et al. |
| 6,395,034 | B1 | 5/2002 | Suddaby |
| 6,402,785 | B1 | 6/2002 | Zdeblick et al. |
| 6,471,724 | B2 | 10/2002 | Zdeblick et al. |
| 6,488,710 | B2 | 12/2002 | Besselink |
| 6,514,260 | B1 | 2/2003 | Zdeblick et al. |
| 6,524,318 | B1 | 2/2003 | Longhini et al. |
| 6,565,574 | B2 | 5/2003 | Michelson |
| 6,575,981 | B1 | 6/2003 | Boyd et al. |
| 6,599,292 | B1 | 7/2003 | Ray |
| 6,626,943 | B2 | 9/2003 | Eberlein et al. |
| 6,648,895 | B2 | 11/2003 | Burkus et al. |
| 6,695,851 | B2 | 2/2004 | Zdeblick et al. |
| 6,706,068 | B2 | 3/2004 | Ferree |
| 6,709,458 | B2 | 3/2004 | Michelson |
| 6,712,818 | B1 | 3/2004 | Michelson |
| 6,712,819 | B2 | 3/2004 | Zucherman et al. |
| 6,712,825 | B2 | 3/2004 | Aebi et al. |
| 6,716,247 | B2 | 4/2004 | Michelson |
| 6,719,794 | B2 | 4/2004 | Gerber et al. |
| 6,723,096 | B1 | 4/2004 | Dorchak et al. |
| 6,730,127 | B2 | 5/2004 | Michelson |
| 6,733,535 | B2 | 5/2004 | Michelson |
| 6,743,234 | B2 | 6/2004 | Burkus et al. |
| 6,746,484 | B1 | 6/2004 | Liu et al. |
| 6,749,636 | B2 | 6/2004 | Michelson |
| 6,758,849 | B1 | 7/2004 | Michelson |
| 6,761,723 | B2 | 7/2004 | Buttermann et al. |
| 6,767,367 | B1 | 7/2004 | Michelson |
| 6,770,074 | B2 | 8/2004 | Michelson |
| 6,773,460 | B2 | 8/2004 | Jackson |
| 6,793,679 | B2 | 9/2004 | Michelson |
| 6,808,537 | B2 | 10/2004 | Michelson |
| 6,814,737 | B2 | 11/2004 | Cauthen |
| 6,814,756 | B1 | 11/2004 | Michelson |
| 6,827,740 | B1 | 12/2004 | Michelson |
| 6,830,570 | B1 | 12/2004 | Frey et al. |
| 6,833,006 | B2 | 12/2004 | Foley et al. |
| 6,835,208 | B2 | 12/2004 | Marchosky |
| 6,849,093 | B2 | 2/2005 | Michelson |
| 6,863,673 | B2 | 3/2005 | Gerbec et al. |
| 6,893,465 | B2 | 5/2005 | Huang |
| 6,902,579 | B2 | 6/2005 | Harms et al. |
| 6,908,485 | B2 | 6/2005 | Crozet et al. |
| 6,932,844 | B2 | 8/2005 | Ralph et al. |
| 6,942,698 | B1 | 9/2005 | Jackson |
| 7,060,073 | B2 | 6/2006 | Frey et al. |
| 7,066,960 | B1 | 6/2006 | Dickman |
| 7,070,598 | B2 | 7/2006 | Lim et al. |
| 7,081,120 | B2 | 7/2006 | Li et al. |
| 7,083,650 | B2 | 8/2006 | Moskowitz et al. |
| 7,084,766 | B2 | 8/2006 | Sayegh et al. |
| 7,087,055 | B2 | 8/2006 | Lim et al. |
| 7,128,760 | B2 | 10/2006 | Michelson |
| 7,163,561 | B2 | 1/2007 | Michelson |
| 7,179,294 | B2 | 2/2007 | Eisermann et al. |
| 7,195,643 | B2 | 3/2007 | Jackson |
| 7,204,853 | B2 | 4/2007 | Gordon et al. |
| 7,208,014 | B2 | 4/2007 | Ralph et al. |
| 7,316,714 | B2 | 1/2008 | Gordon et al. |
| 7,318,839 | B2 | 1/2008 | Malberg et al. |
| 7,326,251 | B2 | 2/2008 | McCombe et al. |
| 2004/0153089 | A1 | 8/2004 | Zdeblick et al. |
| 2004/0210313 | A1 | 10/2004 | Michelson |
| 2004/0230100 | A1 | 11/2004 | Shluzas |
| 2004/0230309 | A1 | 11/2004 | DiMauro et al. |
| 2004/0236331 | A1 | 11/2004 | Michelson |
| 2004/0249388 | A1 | 12/2004 | Michelson |

OTHER PUBLICATIONS

B-Twin Expandable Spinal System, web page (http://www.disc-o-tech.com/Articles/Article.asp?CategoryID=4&ArticleID=74), no date given.

Invitation to Pay Additional Fees pp. 1-4; Annex to Form PCT/ISA 206 pp. 1-3.

Patent Cooperation Treaty, International Search Report, Date completed; Nov. 7, 2006, p. 1-7, ISA, European Patent Office, P.B. 5818 Patentlaan 2 NL—2280 HV Rijswijk.

Patent Cooperation Treaty, International Preliminary Report, Date completed: Dec. 13, 2007, p. 1-20, International Preliminary Examining Authority, European Patent Office—Gitschiner Str. 103 D-10958 Berlin.

Patent Cooperation Treaty, Written Opinion of the International Searching Authority, p. 1-9, ISA, European Patent Office—Gitschiner Str. 103 D-10958 Berlin.

SPINE SURGERY METHOD AND MOTION PRESERVING IMPLANT

This application is a Continuation-In-Part claiming priority from U.S. Ser. No. 11/236,068, entitled SPINE SURGERY METHOD AND IMPLANT, filed Sep. 27, 2005, which is incorporated herein by reference.

I. BACKGROUND OF THE INVENTION

A. Field of Invention

This invention pertains to the art of methods and apparatuses regarding spine surgery and more specifically relates to surgical procedures, associated instrumentation and a motion preserving implant to be positioned within, and in some embodiments deployed within, a vertebral space.

B. Description of the Related Art

The volume of spinal surgeries to treat degenerative disc and facet disease has steadily increased over the past decade, fueled by population demographics and advancements in diagnostic and instrumentation adjuncts. Improvements in intraoperative radiological imaging and surgical technique have generated a great deal of interest in applying minimally invasive surgical (MIS) techniques to spinal applications. As in other surgical subspecialties, it is hoped such minimally invasive techniques applied to spinal surgery will result in less soft tissue trauma, less operative blood loss, reduced operative time, faster recovery periods and lower costs.

Known spinal surgical techniques, though generally working well for their intended purposes, have been adopted from traditional open surgical (non-MIS) techniques. As a result, known spinal surgical methods, instrumentation and interbody implants have disadvantages. One disadvantage is that the physical components are relatively large and bulky. This reduces surgeon visualization of the surgical site. Another disadvantage of know spinal surgical methods is that known surgical tools and implants are cumbersome and difficult to maneuver within the limited surgical space available.

As a result of the aforementioned disadvantages, many intradiscal "fusion" implants have been developed to replace a degenerative disc and to maintain stability of the disc interspace between adjacent vertebrae until a solid arthrodesis has been achieved. These known "interbody fusion devices" have had variable geometries and have been classified by Zdeblick et al. in U.S. Pat. No. 6,695,851 into two basic categories; solid implants and bony ingrowth implants. Examples of solid implants are provided in U.S. Pat. Nos. 4,878,915, 4,743,256, 4,349,921 and 4,714,469. The previously noted patent to Zdeblick et al. (U.S. Pat. No. 6,695,851) as well as U.S. Pat. No. 4,820,305 to Harms et al. are examples of bony ingrowth implant devices. Other types of implants in the interbody fusion device category are provided in the following U.S. Pat. No. 5,397,364 to Kozak; U.S. Pat. No. 5,015,247 to Michelson, U.S. Pat. Nos. 4,878,915, 4,743,256, 4,834,757 and 5,192,327 to Brantigan; U.S. Pat. Nos. 4,961,740 and 5,055,104 to Ray; and 4,501,269 to Bagby.

The devices provided in the aforementioned references all have relatively fixed geometries, most commonly rectangular, trapezoidal, or cylindrical in shape. Jackson, in U.S. Pat. No. 6,773,460, has developed anterior interbody device that is expandable relative to the vertical axis of the intradiscal space. Despite this progression in intradiscal implant geometry, a device having an optimized geometry to provide an optimal vertebral endplate footplate is lacking. A specific surgical method and complementary implant instrumentation system is also lacking. Various surgical methods have been devised for the implantation of interbody fusion devices. Dr. Gary Michelson's technique and associated instruments as provided in U.S. Pat. No. 5,484,437 is but one example. These known techniques along with their associated instruments and implants lack one or more of the criteria for optimal use in anterior, posterior, or transforaminal minimally invasive approaches compatible with currently available minimally invasive spine surgery and/or minimal access spinal techniques (MAST).

The present invention provides methods and apparatuses for overcoming these disadvantages by providing an interbody implant, that in some embodiments provides motion-preserving articulation, that allows for minimally invasive spinal surgery.

II. SUMMARY OF THE INVENTION

According to one embodiment of this invention, an implant comprises: (A) a first member comprising: (1) a first beam having a first limb, a mid-portion, and a second limb; (2) a second beam having a first limb, a mid-portion, and a second limb; (3) a first post having a first end operatively connected to the first limb of the first beam and a second end operatively connected to the first limb of the second beam, the first post having a length defined as the distance between its first and second ends; and, (4) a second post having a first end operatively connected to the second limb of the first beam and a second end operatively connected to the second limb of the second beam, the second post having a length defined as the distance between its first and second ends; (B) a second member that is pivotal with respect to the first member, comprising: (1) a first beam having a first limb, a mid-portion, and a second limb; (2) a second beam having a first limb, a mid-portion, and a second limb; (3) a third post having a first end operatively connected to the first limb of the first beam and a second end operatively connected to the first limb of the second beam, the third post having a length defined as the distance between its first and second ends; and, (4) a fourth post having a first end operatively connected to the second limb of the first beam and a second end operatively connected to the second limb of the second beam, the fourth post having a length defined as the distance between its first and second ends; (C) the first beam of the first member and the first beam of the second member define a first contact surface that contacts the endplate of a first associated vertebral body; (D) the second beam of the first member and the second beam of the second member define a second contact surface that contacts the endplate of a second associated vertebral body; (E) the implant is deployable, when positioned within a vertebral space between the first and second vertebral bodies, from a first non-expanded condition where the first contact surface has a first effective footprint area $A1$ to a second expanded condition where the first contact surface has a second effective footprint area $A2$, the ratio $A2/A1$ is at least 1.05; and, (F) at least one of the first, second, third and fourth posts is length variable in response to a load put on the implant by the first and second associated vertebral bodies after deployment of the implant.

According to another embodiment of this invention, at least two of the first, second, third and fourth posts are length variable in response to the load put on the implant by the first and second vertebral bodies after deployment of the implant.

According to another embodiment of this invention, one of the posts that is length variable is formed of a first viscoelastic material providing a first motion characteristic and the other of the posts that is length variable is formed of a second viscoelastic material providing a second motion characteristic that is substantially different than the first motion characteristic.

According to another embodiment of this invention, the post that is length variable decreases in length in response to a compression load put on the implant by the first and second vertebral bodies after deployment of the implant.

According to another embodiment of this invention, the post that is length variable increases in length in response to a tensile load put on the implant by the first and second vertebral bodies after deployment of the implant.

According to yet another embodiment of this invention, the post that is length variable is formed of a viscoelastic material.

According to another embodiment of this invention, the post that is length variable is also laterally variable in response to a lateral load put on the implant by the first and second associated vertebral bodies after deployment of the implant.

According to still another embodiment of this invention, the post that is length variable comprises a spring that is used to provide the length variation.

According to another embodiment of this invention, the post that is length variable comprises first and second portions separated by a space; the first and second portions move relative to each other as the post that is length variable varies in length; and, at least one spring that is used to provide the length variation is positioned within the space.

According to another embodiment of this invention, (A) the post that is length variable comprises first and second portions separated by a space; (B) the first and second portions move relative to each other as the post that is length variable varies in length; and, (C) a viscoelastic material that is used to provide the length variation is positioned within the space.

According to another embodiment of this invention, (A) the post that is length variable comprises first and second portions separated by a space; (B) the first and second portions move relative to each other as the post that is length variable varies in length; and, (C) a bladder that receives a compressible fluid and that is used to provide the length variation is positioned within the space.

According to still another embodiment of this invention, (A) the post that is length variable comprises first and second portions; (B) the first portion comprises a cavity; and, (C) at least a part of the second portions moves within the cavity as the post that is length variable varies in length.

According to another embodiment of this invention, (A) the mid-portion of the first beam of the first member and the mid-portion of the first beam of the second member are pivotally connected and define a first pivotal connection; (B) the mid-portion of the second beam of the first member and the mid-portion of the second beam of the second member are pivotally connected and define a second pivotal connection; and, (C) the implant further comprises: a fifth post having a first end operatively connected to the first pivotal connection and a second end operatively connected to the second pivotal connection.

According to another embodiment of this invention, the fifth post comprises: (A) a first portion having a proximal end defining the first end of the fifth post and a distal end having a concave surface; (B) a second portion having a proximal end defining the second end of the fifth post and a distal end having a convex surface that engages the concave surface; and, (C) the engagement of the concave surface with the convex surface permits the first portion to pivot with respect to the second portion in response to a load put on the implant by the first and second vertebral bodies after deployment of the implant.

According to another embodiment of this invention, the fifth post has a longitudinal axis that is substantially collinear with the center axis of the implant.

According to another embodiment of this invention, the fifth post is length variable in response to a load put on the implant by the first and second vertebral bodies after deployment of the implant.

According to yet another embodiment of this invention, an implant comprises: (A) a first member comprising: (1) a first beam having a first limb, a mid-portion, and a second limb; (2) a second beam having a first limb, a mid-portion, and a second limb; (3) a first post having a first end operatively connected to the first limb of the first beam and a second end operatively connected to the first limb of the second beam; and, (4) a second post having a first end operatively connected to the second limb of the first beam and a second end operatively connected to the second limb of the second beam; (B) a second member that is pivotal with respect to the first member, comprising: (1) a first beam having a first limb, a mid-portion, and a second limb; (2) a second beam having a first limb, a mid-portion, and a second limb; (3) a third post having a first end operatively connected to the first limb of the first beam and a second end operatively connected to the first limb of the second beam; and, (4) a fourth post having a first end operatively connected to the second limb of the first beam and a second end operatively connected to the second limb of the second beam; (C) the first beam of the first member and the first beam of the second member define a first contact surface that contacts the endplate of a first associated vertebral body; (D) the second beam of the first member and the second beam of the second member define a second contact surface that contacts the endplate of a second associated vertebral body; (E) the implant is deployable, when positioned within a vertebral space between the first and second vertebral bodies, from a first non-expanded condition where the first contact surface has a first effective footprint area A1 to a second expanded condition where the first contact surface has a second effective footprint area A2, the ratio A2/A1 is at least 1.05; and, (F) at least one of the first, second, third and fourth posts is laterally variable in response to a lateral load put on the implant by the first and second associated vertebral bodies after deployment of the implant.

According to another embodiment of this invention, at least two of the first, second, third and fourth posts are laterally variable in response to a lateral load put on the implant by the first and second associated vertebral bodies after deployment of the implant.

According to another embodiment of this invention, the post that is laterally variable is formed of a viscoelastic material.

One advantage of this invention is that the implant has an open profile when fully expanded, maximizing boney ingrowth surface area and bone graft-host contact.

Another advantage of this invention is that the surgeon achieves enhanced visualization of the bone graft-vertebral body endplate interface.

Another advantage of this invention is that the implant allows for minimally invasive deployment via either an anterior, posterior or anterolateral surgical approach.

Another advantage of this invention is that the implant can be used as an interbody fusion device or as a motion-preservation device, either constrained or unconstrained.

Still other benefits and advantages of the invention will become apparent to those skilled in the art to which it pertains upon a reading and understanding of the following detailed specification.

III. BRIEF DESCRIPTION OF THE DRAWINGS

The invention may take physical form in certain parts and arrangement of parts, embodiments of which will be described in detail in this specification and illustrated in the accompanying drawings which form a part hereof and wherein.

IV. DETAILED DESCRIPTION OF THE INVENTION

Figure 1A:
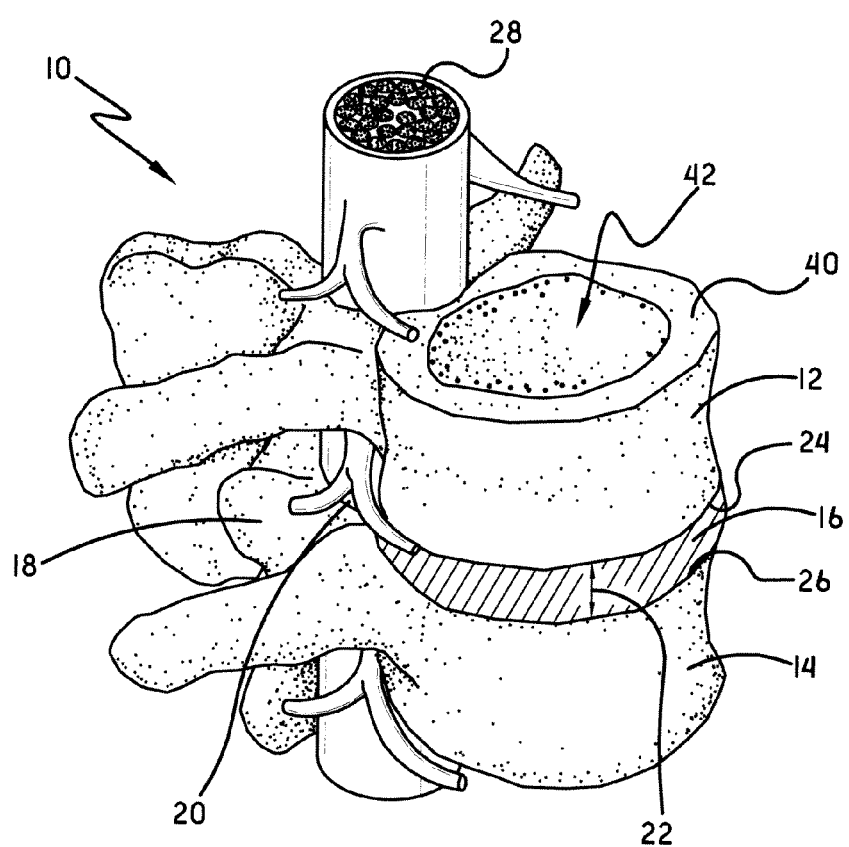
FIG. 1A is a side perspective view of a spinal segment showing a vertebral space defined by the intradiscal space usually occupied by a disc between two adjacent vertebral bodies.

Referring now to the drawings wherein the showings are for purposes of illustrating embodiments of the invention only and not for purposes of limiting the same, the implants of this invention may be inserted within and, in some embodiments deployed within a vertebral space 22. By vertebral space it is meant the space in a spinal column where the implant 100 will be placed. In one embodiment, shown in FIG. 1A, a spinal segment 10 is made up of two vertebrae 12, 14 attached together by ligaments with a disc 16 separating them. Facet joints 18 fit between the two vertebrae 12, 14 and allow for movement. The neural foramen 20 between the vertebrae 12, 14 allow space for the nerve roots to travel freely from the spinal cord 28 to the body. If it is required to remove the disc 16 and replaced it with an implant 100, the space occupied by the disc 16, the intradiscal space between the two adjacent vertebral bodies 12, 14, defines the vertebral space 22. In another embodiment, shown in FIG. 1B, a spinal segment 30 is made up of three vertebrae 32, 34, 36 attached together by ligaments. If it is required to remove the middle vertebra 34 (it is shown diseased) along with the adjacent discs 38, 40, such as may be required because of a corpectomy defect, and replaced them with an implant 100, the space between the two outer vertebral bodies 32, 36, defines the vertebral space 22. It should be understood that these are simply two non-limiting examples of the vertebral space 22 into which an implant 100 can be used according to this invention because any vertebral space chosen with the sound judgment of a person of skill in the art can be used. As the components and operation of a spinal column is well known to those of skill in the art, further detail will not be provided here.

Figure 1B:
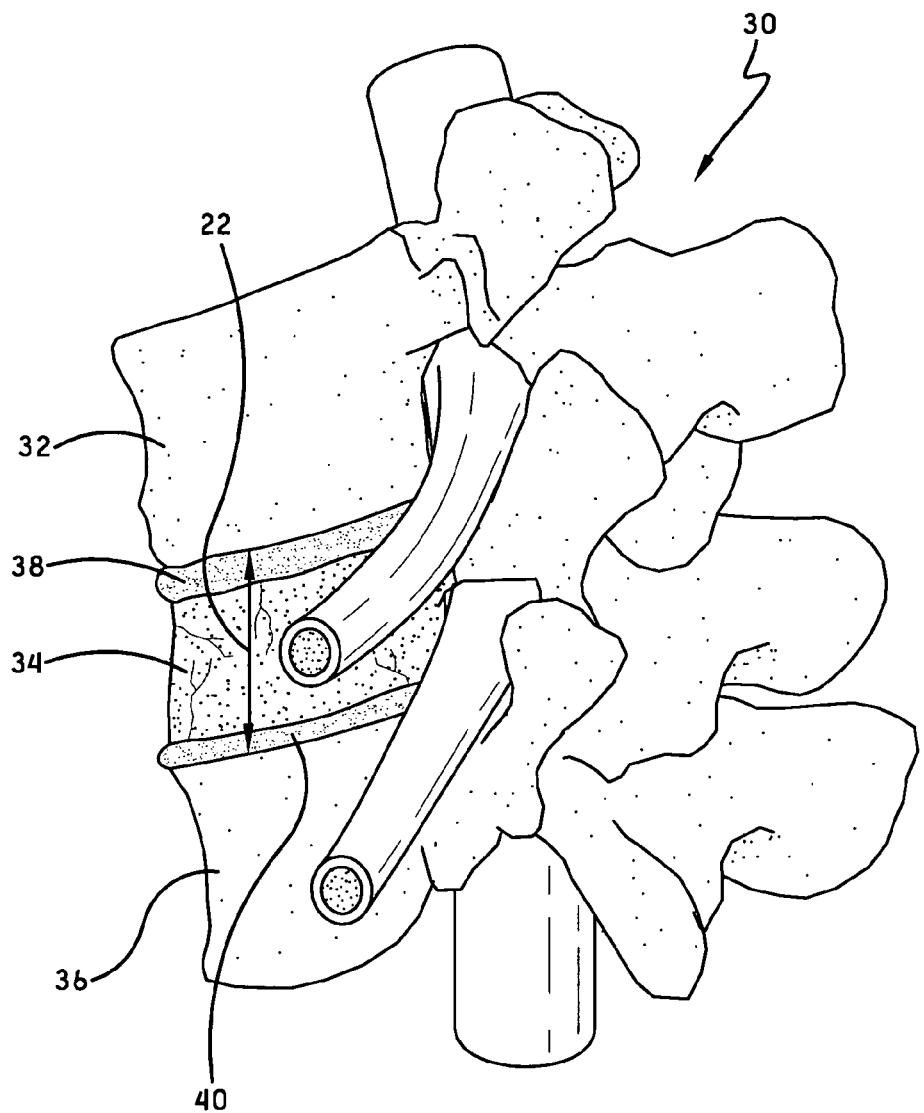
FIG. 1B is a side perspective view of a spinal segment showing a vertebral space defined by the space usually occupied by a vertebral body and its two adjacent discs.
Figure 2:
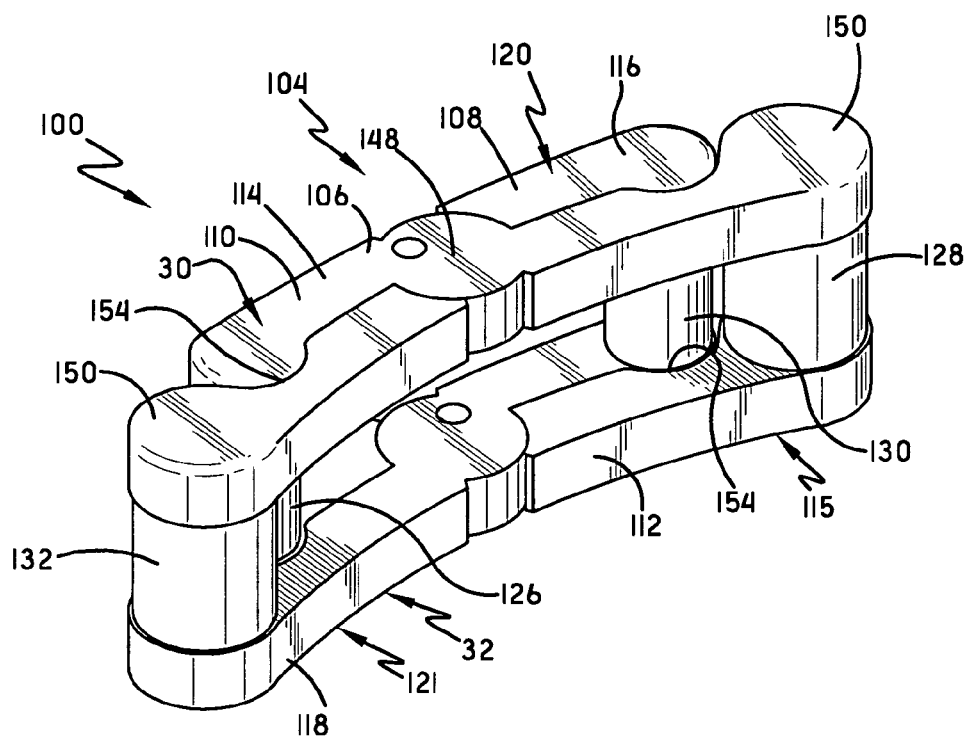
FIG. 2 is a side perspective view of one embodiment of the implant of this invention in the non-expanded, non-deployed condition.
Figure 4:
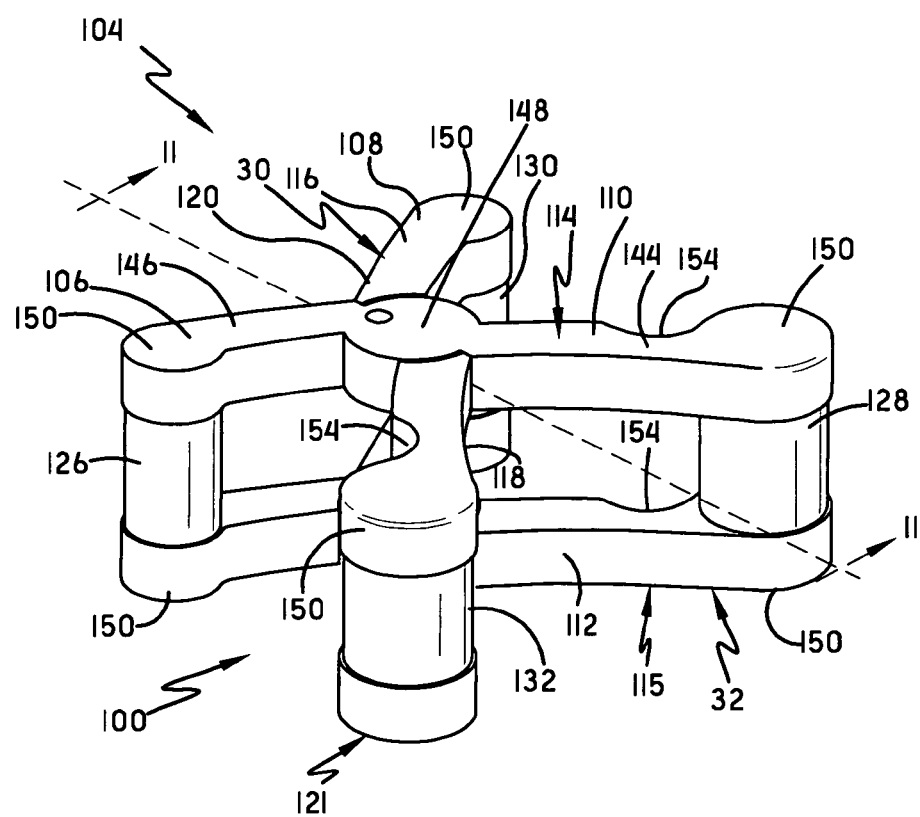
FIG. 4 is a perspective side view of the implant shown in FIGS. 2 and 3 but in the expanded, deployed condition.
Figure 5:
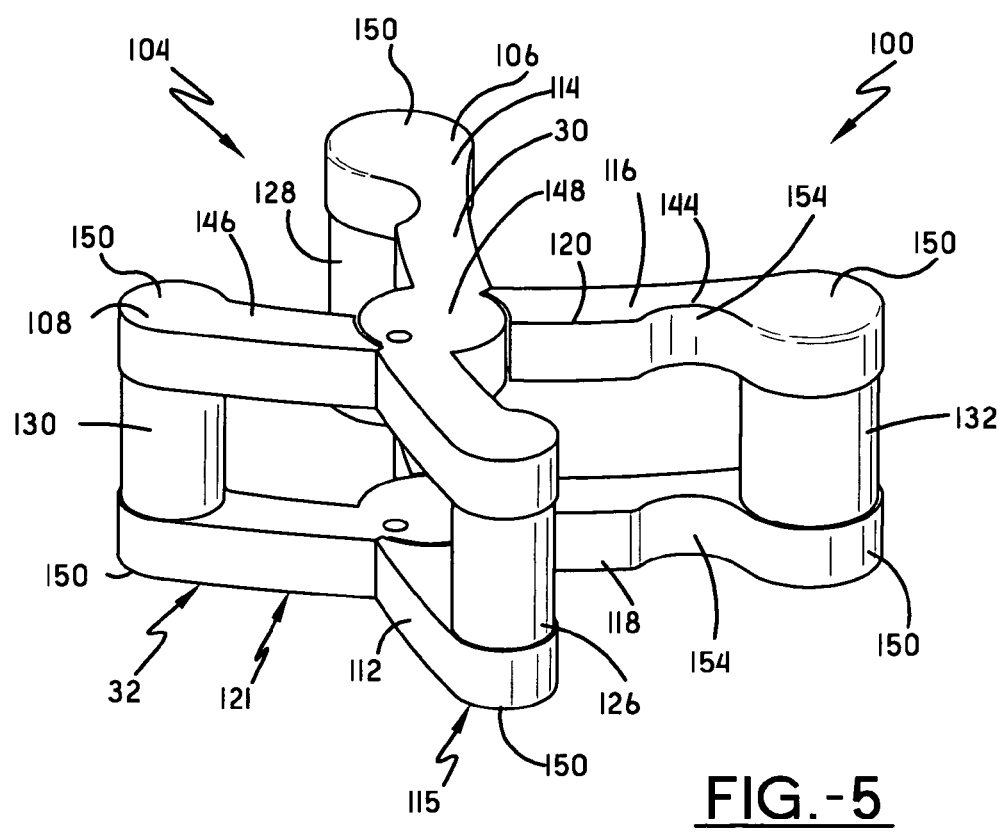
FIG. 5 is a view similar to that shown in FIG. 4, but from another side.

With reference now to FIGS. 1A, 1B, 2 and 4, the implant 100 can be positioned within the vertebral space 22 in a first non-expanded condition, as shown in FIG. 2, and can then be deployed within the vertebral space 22 to a second expanded condition, as shown in FIG. 4. It should be noted that the term "deploy" as used in this patent refers to any adjustment of an implant after the implant has been initially placed into the vetebral space that involves relative motion of one portion of the implant with respect to another portion of the implant. Non-limiting examples of deployment include implants that have one portion that pivots or moves curvilinearly with respect to another portion and implants that have one portion that slides or moves linearly with respect to another portion. Implants that expand in any manner and in any direction fall under the definition of "deploy." This expandable design is very beneficial for the surgeon. When in the non-expanded reduced footprint condition, the implant 100 is small enough to be passed through a standard microdiscectomy type annulotomy, making it truly compatible with minimally invasive surgical (MIS) techniques. Commercially available minimal access spinal retractor systems can be used with minimal requirements for bony resection or soft tissue retraction. Once placed within the vertebral space 22, the implant 100 can be deployed into the expanded condition where it provides a larger effective footprint area. This larger footprint is compatible with more invasive anterior lumbar interbody fusion or bilateral posterior techniques.

Figure 6:
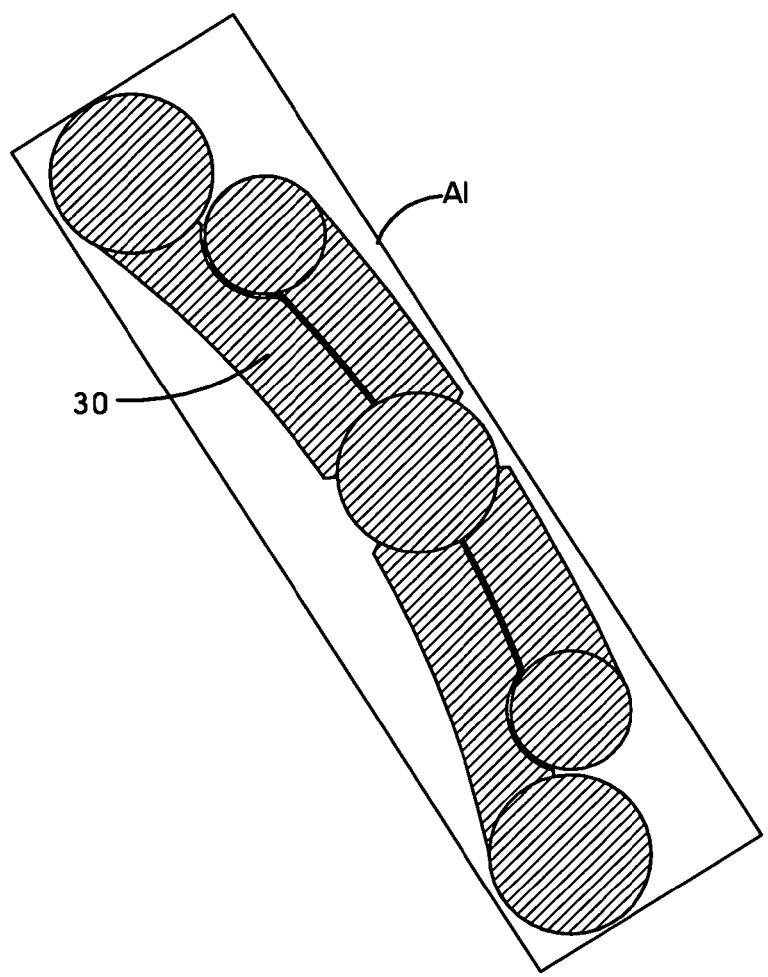
FIG. 6 is a top view illustrating the effective footprint area of the implant when in the non-expanded condition.
Figure 7:
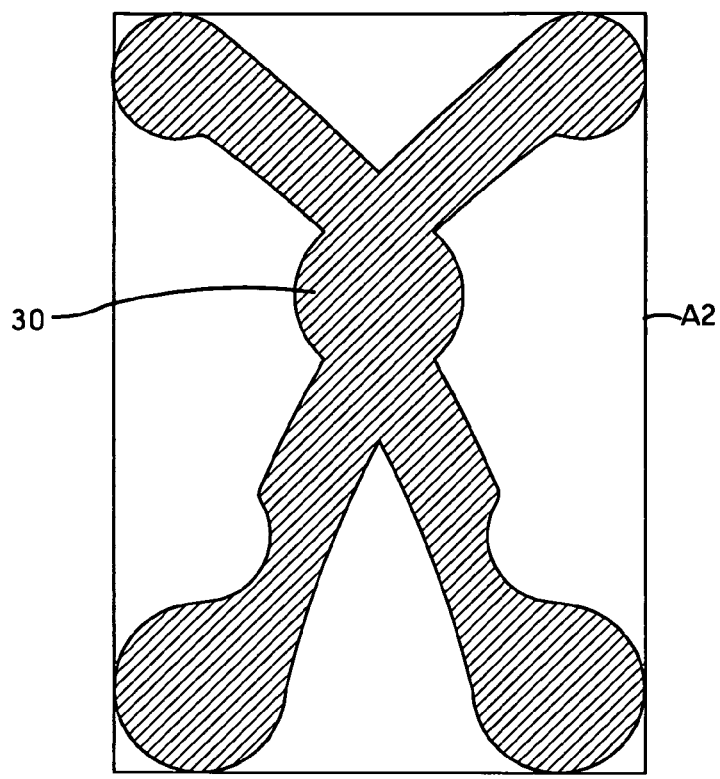
FIG. 7 is a top view similar to that of FIG. 6 but illustrating the effective footprint area of the implant when in the expanded, deployed condition.

With reference now to FIGS. 1A, 1B and 2-7, the implant 100 has a first vertebral body endplate contact surface 30 that provides a first effective footprint area A1, as illustrated in FIG. 6, when in the first non-expanded condition. The first endplate contact surface 30 provides a second effective footprint area A2, as illustrated in FIG. 7, when in the second expanded condition. For purposes of this patent, "effective footprint area" is defined as the area of the smallest rectangle that would encompass or surround the implant vertebral contact surface 30, where the rectangle perimeter contacts the implant 100 contact surface 30 perimeter at a minimum of two points. By "smallest rectangle" it is meant the rectangle having the smallest possible area. Thus, for example, if the implant contact surface 30 was rectangular in shape with a width W and a length L, the effective footprint area would be the area of a rectangle with width W and length L (the effective footprint area would be W times L). If, as another example, the implant contact surface 30 was circular in shape with a diameter D, the effective footprint area would be the area of a square with sides having a length D (the effective footprint area would be D times D). As a general rule, the larger this ratio the easier for the surgeon to place the implant 100 into position while still providing excellent contact with the adjacent vertebrae endplates 24, 26. It is preferred that the ratio A2/A1 is at least 1.05. More preferably, the ratio A2/A1 is at least 1.3 and most preferably the ratio A2/A1 is at least 1.5. For the implant 100 embodiment shown in FIGS. 2-7, the ratio of the second effective foot print area A2 to the first effective foot print area A1, A2/A1 is approximately 1.8.

With reference now to FIGS. 1A, 1B and 2-5, the implant 100 may not only have the first vertebral body endplate contact surface 30 adapted to contact the first vertebral body endplate 24 but also may have a second vertebral body endplate contact surface 32 adapted to contact the second vertebral body endplate 26. Each of the first and second contact surfaces 30, 32 may expand simultaneously from the first effective footprint areas A1 to the second effective footprint areas A2. However, it is also contemplated to only expand one of the contact surfaces 30, 32. The implant 100 may have a first member 106, a second member 108 and a pivotal connection 104 between the first and second members 106, 108. As a result, the second member 108 can be pivoted with respect to the first member 106 from the first non-expanded condition to the second expanded condition. In the embodiment shown, the first member 106 has first and second beams 110, 112 each having outer surfaces 114, 115. Similarly, the second member 108 has first and second beams 116, 118 each having outer surfaces 120, 121. The outer surface 114 of the first beam 110 of the first member 106 and the outer surface 120 of the first beam 116 of the second member 108 define the first contact surface 30. Similarly, the outer surface 115 of the second beam 112 of the first member 106 and the outer surface 121 of the second beam 118 of the second member 108 define the second contact surface 32. These contact surfaces 30, 32 may be serrated/knurled to facilitate cutting into bony endplates to prevent rotation or expulsion of the device by external rotational or flexion-extension forces.

With reference now to FIGS. 1A, 1B and 2-5 and 18, the implant 100 may have first and second posts 126, 128 connecting the first beam 110 of the first member 106 to the second beam 112. Similarly, third and fourth posts 130, 132 may connect the first and second beams 116, 118 of the second member 108. These posts 126, 128, 130, 132 may attach to the beams 110, 112, 116, 118 in any manner chosen with the sound judgment of a person of skill in the art. In one embodiment shown in FIG. 18, however, each post 126, 128, 130, 132 has a dowel member 134 extending from at least one end and in one embodiment, each end. These dowels 134 may be received in openings 135 provided on the inner surfaces 136 of the beams 110, 112, 116, 118. This provides for a secure connection and makes the use of fasteners and adhesives unnecessary. In the embodiment shown, the dowels 134 have a polygonal shape that matches the polygonal shape of the openings 135. This type of connection prevents the posts from rotating with respect to the beams. In another embodiment, the dowels 134 and openings 135 are circular in shape to permit the dowels 134 to rotate within the openings 135. The particular shape of the dowels 134 and openings 135 can be selected based on the sound judgment of a person of skill in the art. In the embodiment shown, each post 126, 128, 130, 132 is positioned at the outer ends of each beam 110, 112, 116, 118. This embodiment provides maximum compression loading characteristics at the area most likely to carry such a load; namely, with reference to FIG. 1, at the outer rim 40 of each vertebrae endplate 42. It should be noted, however, that depending on the particular use, the number of posts used and their positions can be varied in accordance with the load requirements across the beams and sound engineering principles. In another embodiment, one or more washer members (not shown), having openings that receive the dowels 134, may be used to extend the height of an individual post for a specific surgical need.

Figure 3:
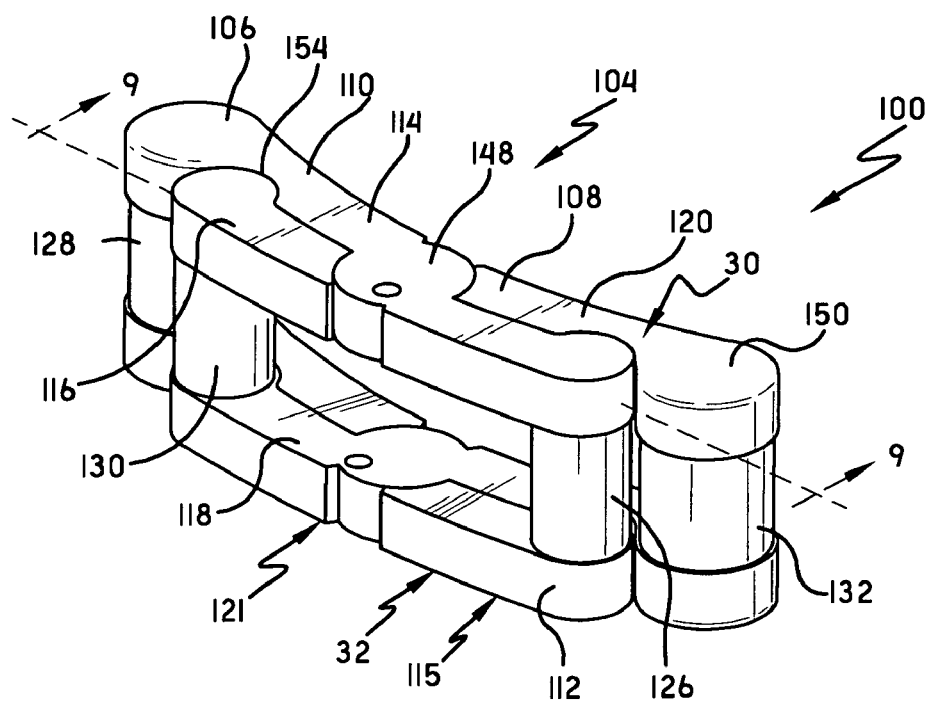
FIG. 3 is a view similar to that shown in FIG. 2, but from the opposite side.
Figure 19:
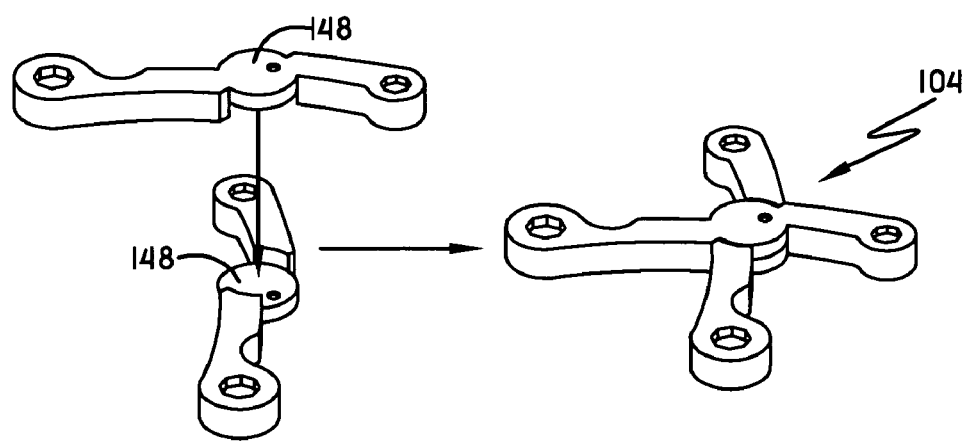
FIG. 19 is an assembly drawing illustrating one embodiment of how the mid-portion of one beam may be juxtaposed to the mid-portion of another beam to form a pivotal connection.

With reference to FIGS. 1A, 1B and 2-5, each beam may have first and second limbs 144, 146 extending from a mid-portion 148. The pods 150 may be defined at the ends of each limb 144, 146. The pods 150 may be flared relative to the width of the limbs 144, 146. They also may be bulbous with the ends being tapered with a chamfer type profile to facilitate advancement and deployment of the implant 100 within the vertebral space 22 and to match the anatomical concave rim 40 of a typical vertebral body endplate 42 shown in FIG. 1A. Each beam may have one limb 144 that is longer than the opposite limb 146. In a more specific embodiment, the extra length is equal to the width of a single pod 150, as shown. The longer limb 144 may have a groove 154 that receives the pod 150 in the opposite beam, as shown. This design provides for easy nesting of the first and second members 106, 108 as shown in FIGS. 2 and 3. This nesting minimizes the overall width of the implant 100 and, thus, is advantageous when inserting the implant 100 into the vertebral space 22, yet permits maximal surface area to the pods 150. Note that the tapered pods 150 are most likely the primary portions of the implant 100 that bear the axial, compressive loading. In one embodiment, the mid-portions 148 of each beam may have a circular cross-section, as shown. Juxtaposing the circular mid-portion 148 of one beam 110 with the adjacent beam 116, as illustrated in FIG. 19, creates the pivotal connection 104 according to one embodiment. This pivotal connection 104 provides for easy manipulation of the implant 100 from the first non-expanded condition into the deployed, expanded condition. This arrangement also makes additional fasteners, pivot pins, bearings and the like unnecessary. This provides for an implant that is easy to manufacture and easy to deploy. The first member 106 may be substantially parallel to the second member 108 when the implant 100 is in the first non-expanded condition. This minimizes the space requirements for the implant 100. In one embodiment, the first and second members 106, 108 are curvilinear in shape, as shown. This curvilinear shape provides procedural options for the surgeon. The surgeon may, for example, use a vertically oriented posterior lumbar interbody fusion technique (PLIF) or may use a transforaminal interbody fusion technique (TLIF). The particular radii of curvature can be selected based on preoperative and intraoperative templating.

Figure 9:
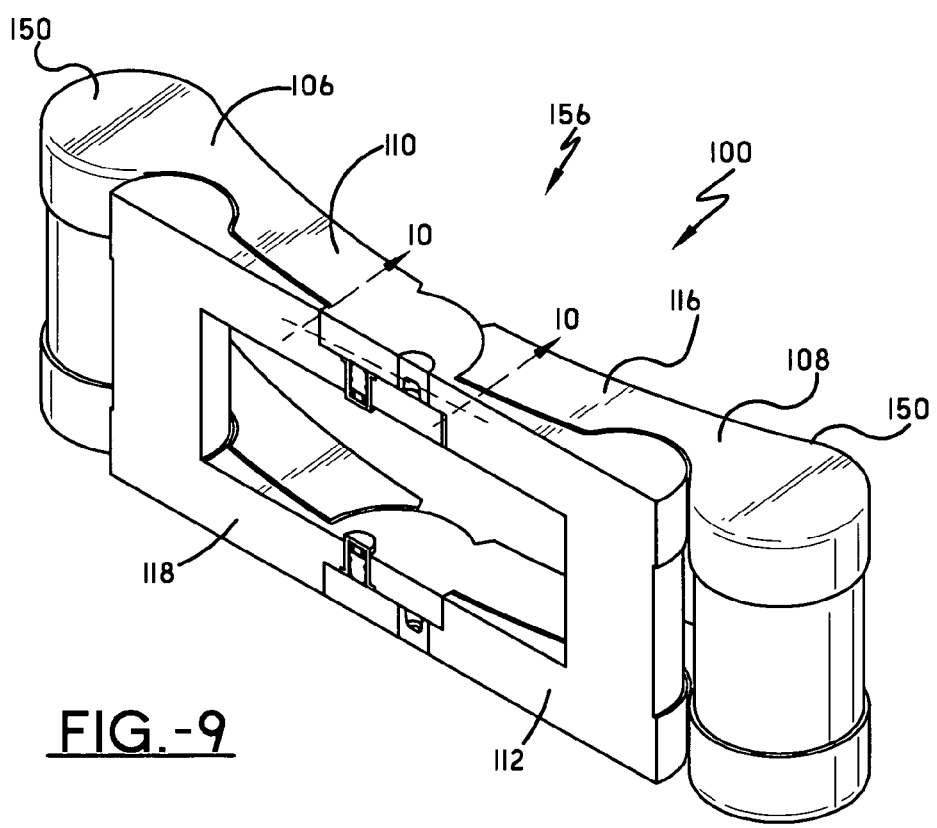
FIG. 9 is a sectional view taken along the line 9-9 of FIG. 3 illustrating the locking mechanism in an unlocked condition.
Figure 10:
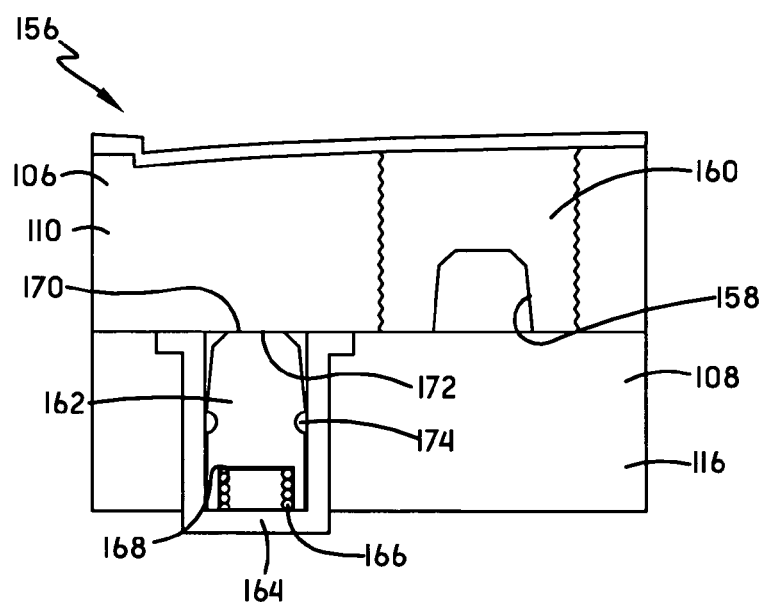
FIG. 10 is an exploded view taken along the lines 10-10 of FIG. 9 and illustrating more details of the locking mechanism.
Figure 11:
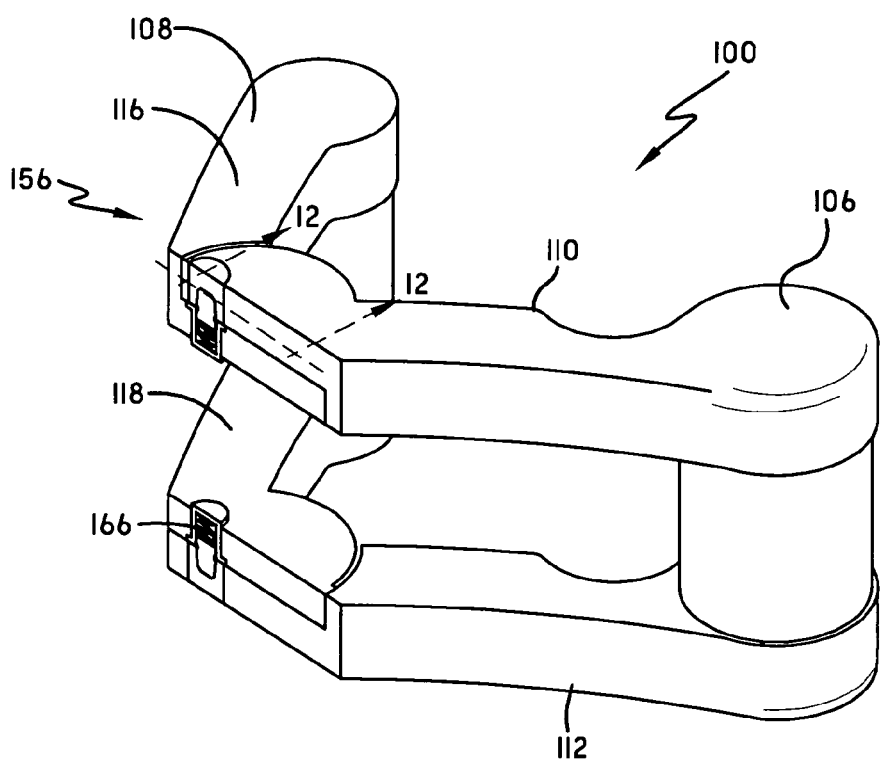
FIG. 11 is a sectional view taken along the line 11-11 from FIG. 4 and illustrating the locking mechanism in a locked condition.
Figure 12:
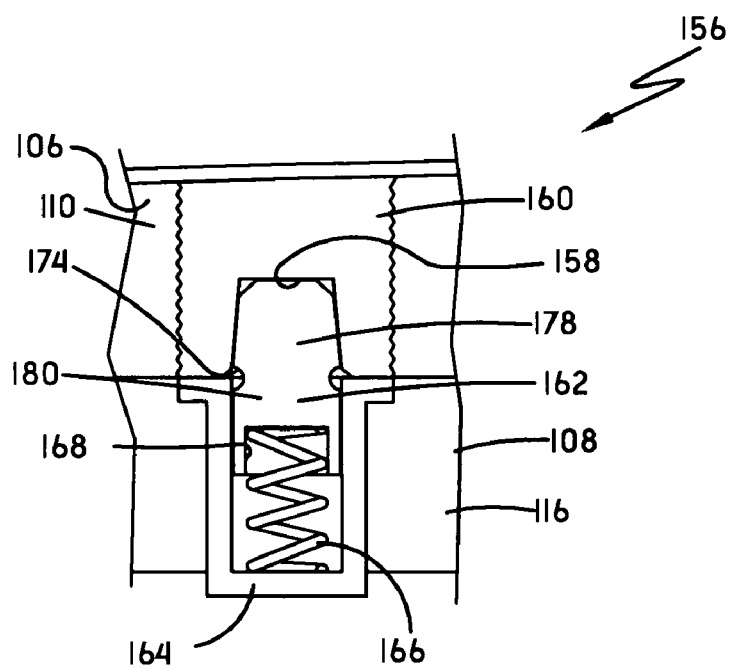
FIG. 12 is an exploded view taken along the lines 12-12 in FIG. 11 and illustrating more details of the locking mechanism in the locked condition.

With reference now to FIGS. 9-12, a locking mechanism 156 may be used to lock the position of the second member 108 with respect to the first member 106 and thereby lock the implant 100 in the second expanded condition. While the particular design for the locking mechanism 156 can be any chosen with the sound judgment of a person of skill in the art, in the embodiment shown a first opening 158 is formed in the first beam 110 of the first member 106. This opening can be formed in any manner chosen with the sound judgment of a person of skill in the art. For the embodiment shown, a threaded plug 160 is received in the beam 110 and contains the first opening 158. A first pin 162 may be positioned in the first beam 116 of the second member 108. This pin 162 may also be positioned within the second member 108 in any well chosen manner. In the embodiment shown, a generally cylindrical cup portion 164 is received within the second member 108. Within the cup portion 164 a biasing means, a spring 166 in one embodiment, is positioned as shown. The pin 162 has a chamber 168 that receives the spring 166. As shown, the pin 162 when fully received within the cup 164 compresses the spring 166 and the pin's upper surface 170 contacts the inner surface 172 of the first member 106. In this way, when in the unlocked condition, the pin 162 is held in place within the cup member 164. As can be seen in FIGS. 9 and 10, the pin 162 and the opening 158 are not in axial alignment when the implant 100 is in the non-expanded condition. In fact, they intentionally are held out of alignment through the pivoting action from the non-expanded condition until the fully expanded condition or fully deployment is reached. This is shown in FIGS. 11 and 12. In this position, the pin 162 is aligned with the opening 158 and thus the biasing force from the spring 166 forces the pin 162 into the opening 158. It should be noted that this insertion of the pin 162 into the opening 158 occurs automatically when the second member 108 is pivoted relative to the first member 106 to a predetermined degree. The particular degree can be varied depending on the needs of the surgeon. Once the pivoting angle is reached, the pin is received within the opening 158 as shown in FIG. 12. In this condition, the second member 108 cannot be pivoted relative to the first member 106.

With continuing reference to FIGS. 9-12, in the event that the surgeon needs to replace the implant 100 or otherwise remove it, it is necessary to return the implant 100 back to the non-expanded condition. To accomplish this, note that the first pin 162 can be broken, and more preferably sheared, into two pieces so that the first and second members 106, 108 can be pivoted back to the non-expanded condition. In the embodiment shown, the pin 162 has a channel 174. As seen best in FIG. 12, this channel 174 is formed in the outer surface of the pin 162 and is axially positioned such that its center is coplanar with the interface of the first and second member 106, 108. As a result of this design, should the surgeon need to unlock the locking mechanism 156 the surgeon need only exert sufficient force on the pin 162 to shear it at the channel 174. Note that the depth of the channel 174 can be varied to vary the torque required to shear the pin 162. Note also that this design provides that upon shearing of the pin 162, the top portion 178 of the pin 162 remains in the opening 158 while the bottom portion 180 of the pin 162 remains in the cup member 164. As a result, both portions of the sheared pin 162 remain confined within the implant 100 and thus will not be inadvertently left within the vertebral space 22 when the implant 100 is removed.

With reference to FIGS. 2 and 4, the method used by the surgeon to deploy the implant 100 can be any that permits the surgeon to pivot the first member 106 with respect to the second member 108 within the limited vertebral space 22. In one embodiment, the surgeon can use a conventional inserter and/or distractor (neither tool shown) to deploy the implant 100.

In another embodiment, shown in FIGS. 20-23, a cable 200 may be used to deploy the implant 100. The cable 200 may extend between a post on the first member 106 and a post on the second member 108. For the embodiment shown, the second post 128 of the first member 106 has first and second cable cavities 202, 204 and the fourth post 132 of the second member 108 has a third cable cavity 206. The first cable cavity 202 may be positioned above the second cable cavity 204 along the axis of the second post 128 as shown. The cable 200 may include an enlarged section 210 with an outer diameter greater than the diameter of the third cable cavity 206 yet smaller than the diameter of the first cable cavity 202 for reasons to be discussed below. The cable 200 may be inserted within the cable cavities as shown with the enlarged section 210 positioned between the first cable cavity 202 and the third cable cavity 206.

Figure 20:
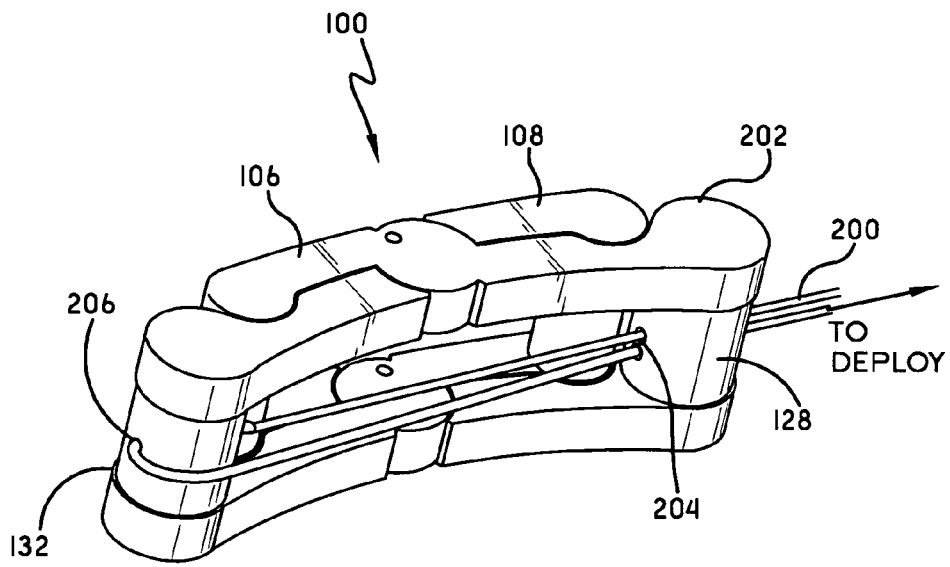
FIG. 20 is a side perspective view of the implant in the non-expanded, non-deployed condition similar to that shown in FIG. 2 but showing the cable that may be used to deploy the implant.
Figure 21:
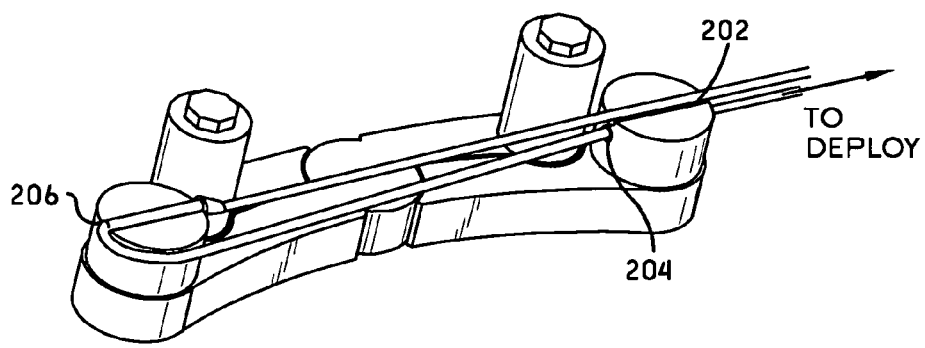
FIG. 21 is a view similar to that shown in FIG. 20 but with the top beams removed to show how the cable is received within the posts.
Figure 22:
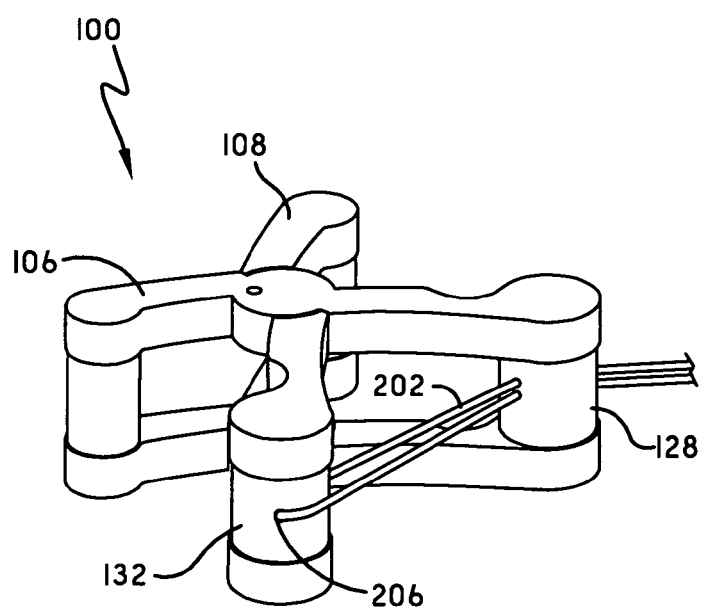
FIG. 22 is a view similar to that shown in FIG. 20 but with the implant in the deployed condition.
Figure 23:
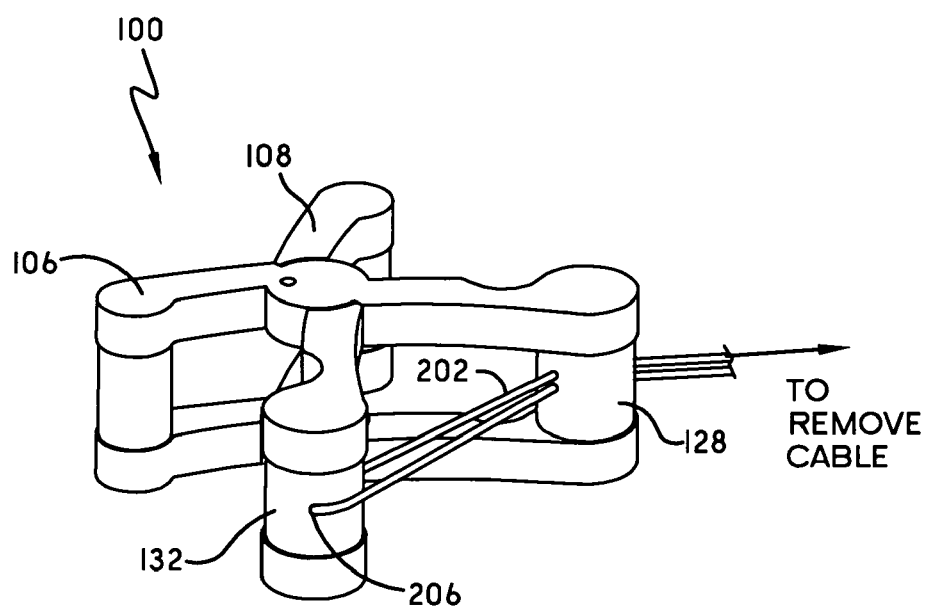
FIG. 23 is a perspective view similar to that shown in FIG. 22 but illustrating how the cable can be removed.

With continuing reference to FIGS. 20-23, deployment of the implant 100 from the first non-expanded condition, shown in FIG. 20, to the second expanded condition, shown in FIG. 22, will now be described. All the surgeon needs to do is apply tension to the cable 200 as indicated by the arrows in FIGS. 20 and 21. This tension begins to pull the cable 200 through the second and third cable cavities 204, 206. Linear motion of the cable 200 soon stops, however, because the enlarged section 210 engages the third cable cavity 206 due to the difference in diameter noted above. At this point, continued application of tension to the cable 200 causes the second member 108 to pivot with respect to the first member 106 and thus causes the implant 100 achieve the expanded condition, shown in FIG. 22. After deployment of the implant 100, the surgeon may, if necessary, apply additional tension to the cable to better position the implant 100 within the vertebral space. To remove the cable 200, it is only necessary for the surgeon to apply tension to the opposite end of the cable 200, as shown in FIG. 23. This tension causes the enlarged section 210 to pass through the first cable cavity 202 due to the difference in diameter noted above. The rest of the cable easily passes through all three cavities 202, 204, 206 as necessary, and the cable 200 is thereby easily removed.

With continuing reference to FIGS. 20-23, it should be noted that the inventor contemplates various design modifications to the embodiment. For example, other posts than those illustrated could be used to receive the cable 200. It should also be noted that the particular position and orientation of the cavities 202, 204, 206 can vary within the sound judgment of a person of skill in the art. Thus, it is not necessary that the cavities 202, 204, 206 be formed through the center of the posts 126, 128. It is also not necessary for the cavities 202, 204, 206 to lie on a plane perpendicular to the axes of the posts 126, 128 as shown. It is also not necessary that the cable 200 and the cavities 202, 204, 206 have circular cross sections as they could be of any shape chosen with the sound judgment of a person of skill in the art. It is also contemplated to use any of a number of ways of achieving the enlarged section 210 of the cable 200. For instance, a separate piece such as a washer could be attached to the cable 200 at that point and serve to prevent the cable 200 from being received within the third cable cavity 206.

Figure 13:
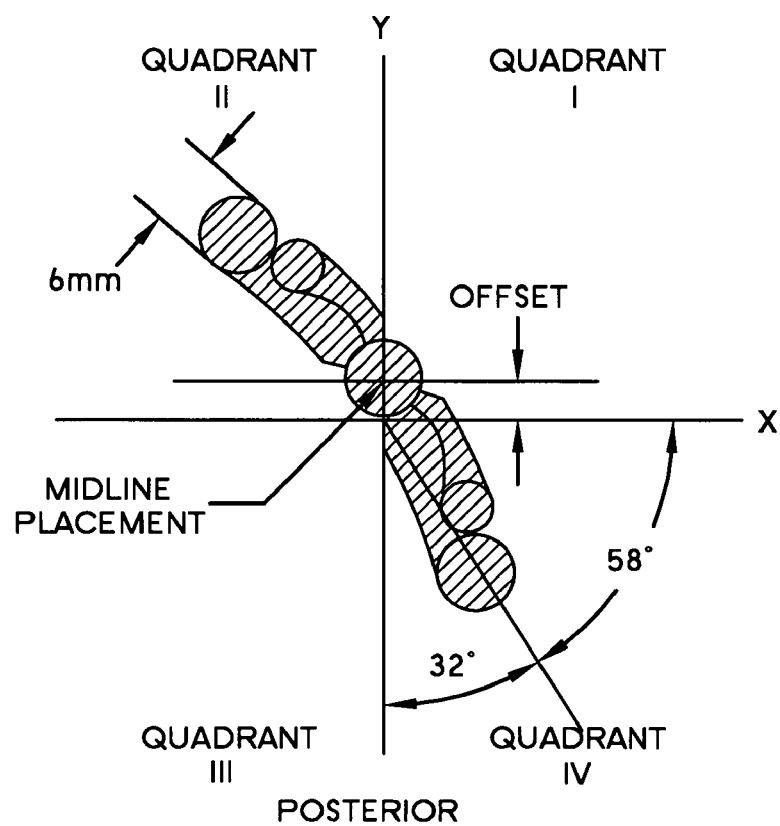
FIG. 13 is a top view of the implant in the non-expanded, non-deployed condition and aligned in a four quadrant system.
Figure 14:
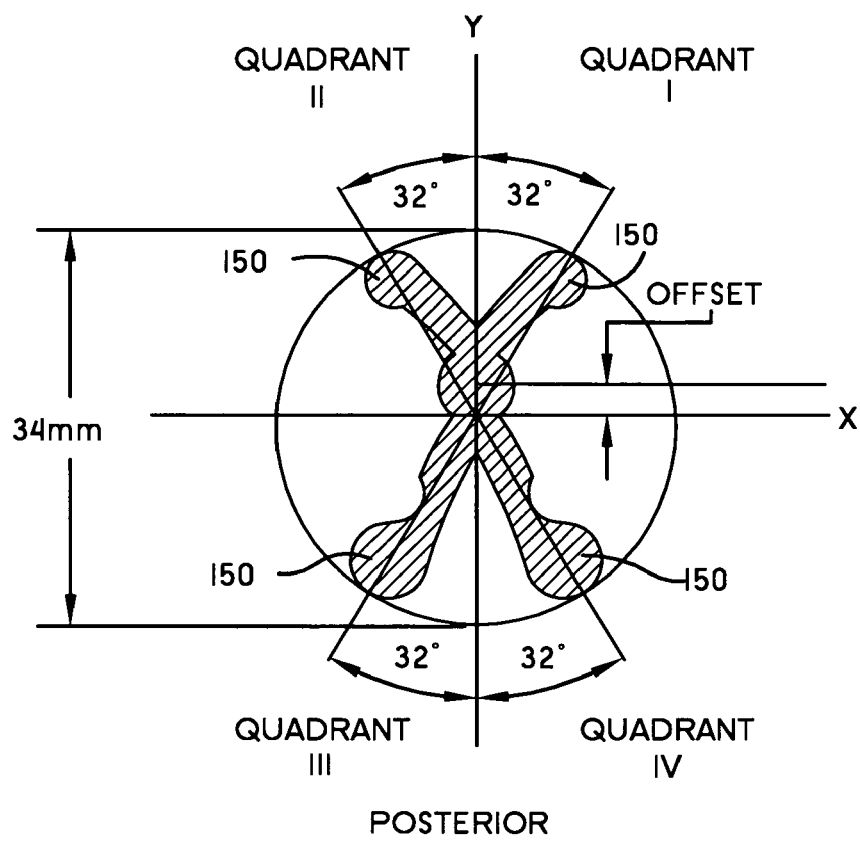
FIG. 14 is a view similar to that shown in FIG. 13, but with the implant shown in the expanded, deployed condition.

With reference now to FIGS. 1A, 1B, 2, 4, 13 and 14, to assist in understanding how the implant 100 may be inserted, aligned and deployed with respect to the vertebral space 22, it is helpful to illustrate the implant 100 in a four quadrant system, labeled Quadrants I, II, III and IV. FIG. 13 shows the implant 100 in the first non-expanded condition and FIG. 14 shows the implant 100 in the second expanded or deployed condition. When in the expanded condition, the implant 100 lies in all four quadrants, with one pod 150 positioned in each quadrant. The location of the pods 150 within their respective quadrants is dependent on the radii of curvature of the implant 100 and also on the overall length, or sizing of the implant 100. The particular radius of curvature for an implant is variable, selected on the basis of preoperative templating and confirmed and/or amended by intraoperative measurements using needle-tipped sounds and intraoperative biplanar fluoroscopic imaging. To insert the implant 100 using a posterior/posterolateral entry passage, see FIG. 13, the implant 100 is placed into quadrant IV and on into the center of the vertebral space 22. The implant 100 is advanced past the midpoint of the vertebral space 22 with an off-set OS1 in the Y-axis direction but centered in the midline, about the Y-axis, as shown. Once placed in this position, the implant 100 can be deployed so that the pods 150 and limbs 144, 146 of the second member 104 migrate away from the pods 150 and limbs 144, 146 of the first member 102 in a scissor-like action. The trailing limb in quadrant IV (for a right sided posterior entry to the disc space) is where the inserter is affixed, holding this limb 144, 146 along the axis of rotation. Full deployment of the implant 100 is achieved when the central axis has locked via the locking mechanism 156 as described above.

With reference now to FIGS. 1A, 1B, and 2-5, the basic surgical technique for placing the implant 100 as an interbody fusion device into a vertebral space 22 using minimally invasive surgical (MIS) techniques will now be described. In this technique the vertebral space 22 may be approached using universally accepted methods for either anterolateral, posterior, or posterolateral (transforaminal) discectomy. Because the implant 100 has such a small, nondeployed (non-expanded) profile, formal facetectomy does not need to be done in order for either an oblique or coronal orientation of the implant 100 within the vertebral space 22. Assuming a standard approach to the posterior/posterolateral annulus of the targeted disc, appropriate retraction of the neighboring neural structures is accomplished with universally available nerve root retractors. For a posterior/posterolateral approach this would include retraction of the dural sac towards the midline and retraction of the adjacent cephalad and caudad nerve roots, as would normally be done for routine discectomy. Upon isolating the annular surface of the targeted disc or discs, variable needle sounds are placed in the vertebral space 22 with a range of radii of curvature. The range of these sounds would have been selected on the basis of pre-operative templating of available imaging studies, including plain radiographs, CT or MRI imaging. This preoperative templating provides a narrower range of radii for intraoperative confirmation, decreasing trial and error sounding. The objective of this intraoperative needle sound placement is to locate the center of the vertebral space 22 and the optimal radii of curvature for the implant 100. The placement of this sound would be confirmed via biplanar intraoperative fluoroscopic imaging. Once the surgeon is satisfied with the centralization and radii of curvature of the needle tipped sound, the radii of curvature of the implant 100 is determined. Routine discectomy is carried out using universally accepted instruments.

With continuing reference to FIGS. 1A, 1B, and 2-5, the vertebral space 22 is then initially distracted with short, straight interbody spacers, progressively sized until sufficient annular tension is achieved. Once this point is reached, longer, variable radii, curvilinear box chisels may be advanced into the vertebral space 22 to remove disc material and cartilaginous endplate. If necessary, one or more discs and one or more vertebrae may be removed. Once a majority of intradiscal material is removed, an endplate cutter may be advanced to the entry point to make graduated cuts in the periphery of the endplate to remove the previously referenced normal concave tapering of the bony endplate towards the periphery of the vertebrae. This process would insure true distraction of the vertebral space 22 from the center. A central distractor is then placed and distraction to the selected level of annular tension is achieved. The degree of this distraction would be based on surgeon preference and/or the vertebral space 22 height of neighboring non-degenerative discs. With this optimal distraction, further discectomy, or removal of disc material, may be accomplished. The distractor is then placed at the presumed center of the vertebral space 22 and centralized placement confirmed by intraoperative fluoroscopic imaging. Adjustments, if necessary, may be made in anterior-posterior and medial-lateral orientation until centralization of the distractor is confirmed.

Still referring to FIGS. 1A, 1B and 2-5, trial spacers of variable heights may then placed with the vertebral space 22 to select the implant 100 height. Alternatively, the implant height could be selected on the basis of preoperative templating and/or directly from the caliper gauge of the distractor. The implant 100 is then selected corresponding to the radii of curvature of the intraoperative needle tipped sounds, the distractor tips and the trial spacer height. The length of the implant 100 is selected on the basis of surgeon preference and/or operative templating. Once the appropriate sized implant 100 is selected, it is affixed to the inserter handle at one of its ends in the non-expanded, nested, non-deployed state and moved to the vertebral space 22. Both the central distractor and the inserter may be color-coded and etched with markings corresponding to the selected sizes. The implant 100 may then be impacted into the vertebral space 22 until the markings are aligned, indicating full seating of the implant 100. Biplanar fluoroscopic imaging may be used to confirm placement of the distractor and full seating of the implant 100. Adjustments, if necessary, can be made at this time by adjusting the amount of distraction and/or orientation of the distractor in the axial or frontal planes, in a manner described above.

With reference now to FIGS. 1A, 1B, 2-5, 13-14 and 20-23, once full seating of the implant 100 in the midline is confirmed (with the previously described off-set OS1 if necessary), the implant 100 is deployed into the expanded condition having a second, larger effective footprint area A1/A2. Deployment may be accomplished by applying tension to the cable 200 and thereby pivoting the second member 108 with respect to the first member 106. Alternatively, deployment may be accomplished by impacting a leading edge of the implant 100, along its central axis. Once the second member 108 is pivoted the sufficient distance for the particular implant 100, the locking mechanism 156 automatically engages and the second member 108 is locked in place with respect to the first member 106. At this point, confirmation of satisfactory implant 100 alignment within the vertebral space 22 may be confirmed by intraoperative biplanar fluoroscopic imaging. Adjustments, if necessary, can be made at this time by changing the degree of distraction and medial-lateral and anterior-posterior translation of the implant 100 by impaction/retraction or rotation with the inserter still in place. Impaction of the distractor against the implant 100 would cause rotation of the implant 100 along its central axis to effect changes in alignment relative to the initial entry angle of the distractor tips, giving the surgeon wide-latitude in final positioning of the implant 100.

With reference now to FIGS. 1A, 1B and 2-8, once satisfactory implant 100 alignment is achieved, the distractor is released and removed and the inserter disengaged. With the implant 100 now in its fully expanded, deployed state, bone grafting is completed by packing in the open profile of the implant 100. An end cap, formed of silicon or other appropriate material, that affixes to the inserter may then be impacted on the trailing limbs of the implant 100 to prevent migration of bone graft/synthetic bone graft and/or other non-specified osteobiologic materials back into the spinal cord 28 area. This completes the contemplated procedure for implantation of the implant 100. If gross mal-position of the implant 100 were encountered or removal otherwise necessary, the procedure would be reversed and the inserter placed back on the implant 100. Once the inserter is back in place, a removal tool that engages the leading edge of the implant 100 and locks back to the trailing limb at the inserter is used to compress and cause shearing of the pin(s), collapsing the implant 100 back into its non-expanded, non-deployed state. The implant 100 could then be removed with a slap hammer attached to the inserter handle, facilitated if necessary by insertion into the vertebral space 22 of the central distractor.

Figure 15:
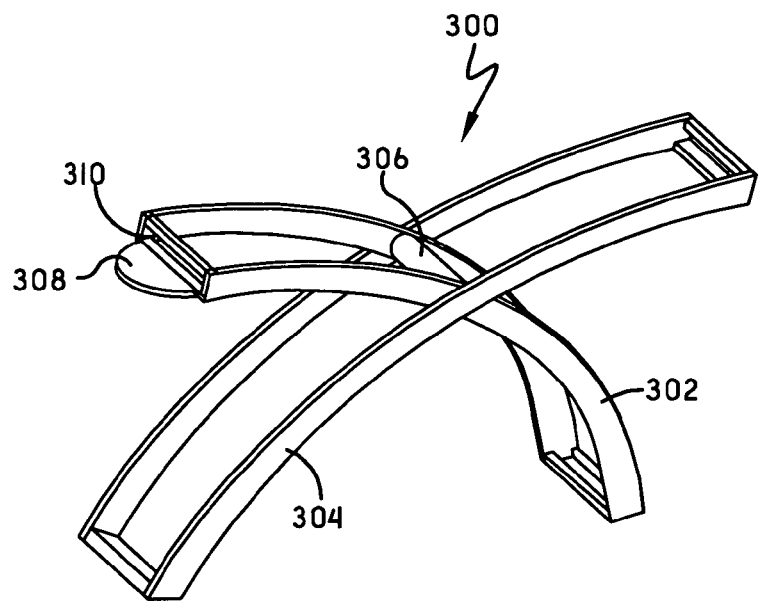
FIG. 15 is a perspective view of an alternate implant embodiment shown in an expanded, deployed condition.

With reference now to FIG. 15, an alternate embodiment for an implant 300 is illustrated. The basic operation of this implant 300 is similar the previously described implant 100 in that a first member 302 is pivotal with respect to a second member 304 from a non-expanded condition, to the deployed, expanded condition, shown in FIG. 15. Thus, only the important differences will be discussed. Note first, that for this implant 300 the first member 302 pivots with respect to the second member 304 about a pivot post 306 that may be centrally located, as shown. Note also that the trailing edge of the first member 302 may include a tip or tab 308 and a slot 310. The surgeon may use an inserter or distractor of conventional design to engage the tab 308 and/or slot 310 and thereby deploy the implant 300.

With reference now to FIGS. 16a, 16b, 16c and 17, another alternate embodiment implant 400 illustrated. As with the earlier described embodiments, this embodiment also includes a first member 402 which is pivotal with respect to a second member 404 from a non-deployed or closed condition (shown in FIG. 16a) to a fully deployed, expanded condition (shown in FIG. 16c). For this embodiment the outer surfaces 406 of the first member 402 are spaced inwardly from the outer surfaces 408 of the second member 404 when the implant 400 is in the non-expanded condition. This provides for a very efficient nesting and greatly reduces the width of the implant 400. The second member 404 may include a pair of beams 410, 410 each having a mid-section 412, as shown, connected together with a pair of walls 414, 414. The walls 414, 414 may be positioned at the outer ends of the beams 410 and may be curved to match the shape of the outer ends of the beams 410, as shown.

With continuing reference to FIGS. 16a, 16b, 16c and 17, the first member 402 may include a pair of beams 416, 416 each having a mid-section 418. The beams 416, 416 may be connected together with a pair of posts 420 fixed at one end to one beam 416 and having opposite ends received within openings formed in receiving members 422, 422 extending from the opposite beam 416, as shown. The posts 420 may be spring loaded to urge the beams 416, 416 away from each other. The ends of the beams 416, 416 may have cut out sections 424 to receive the walls 414 when the implant 400 is in the non-expanded condition. This improves the nesting capabilities of the implant 400. The mid-sections 412 of the beams 410 may have notches 426 facing toward the beams 416 and the mid-sections 418 of the beams 416 may have notches 428 facing toward the beams 410, as shown. The purpose for these notches 426, 428 will be described further below. The mid-sections 412, 418 may also have holes 430 formed therethrough. These holes 430 reduce the material necessary to form the beams 410, 416 and also provide additional space to add bone graft material after the implant 400 has been deployed.

Figure 16A:
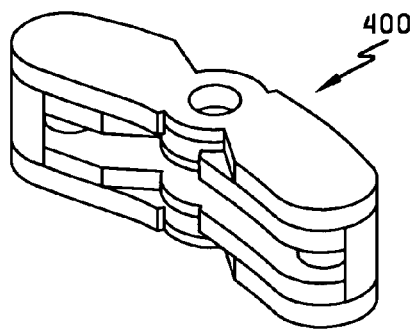
FIG. 16a shows an alternate embodiment implant in a non-expanded, non-deployed condition.
Figure 16B:
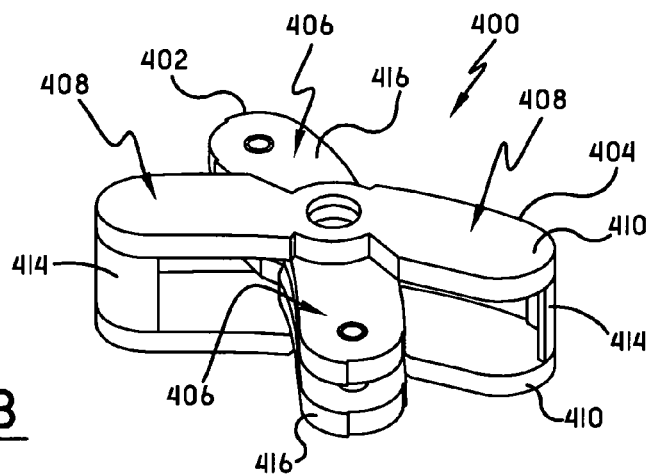
FIG. 16b shows the implant of FIG. 16a in a first stage of deployment.
Figure 16C:
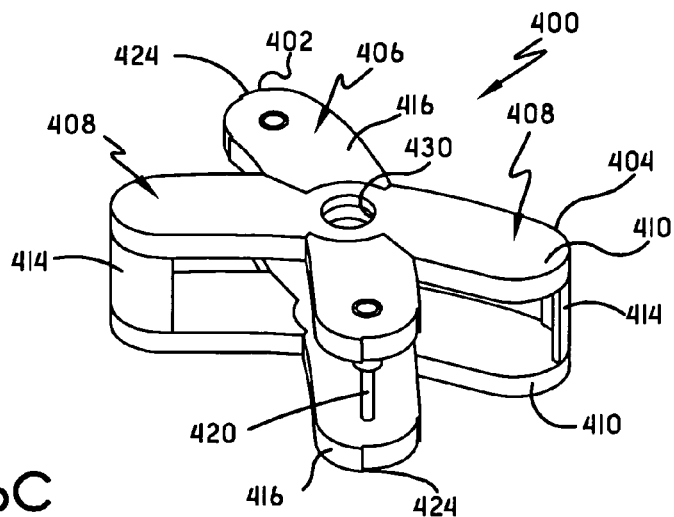
FIG. 16c shows the implant of FIGS. 16a and 16b in the expanded, fully deployed condition.
Figure 17:
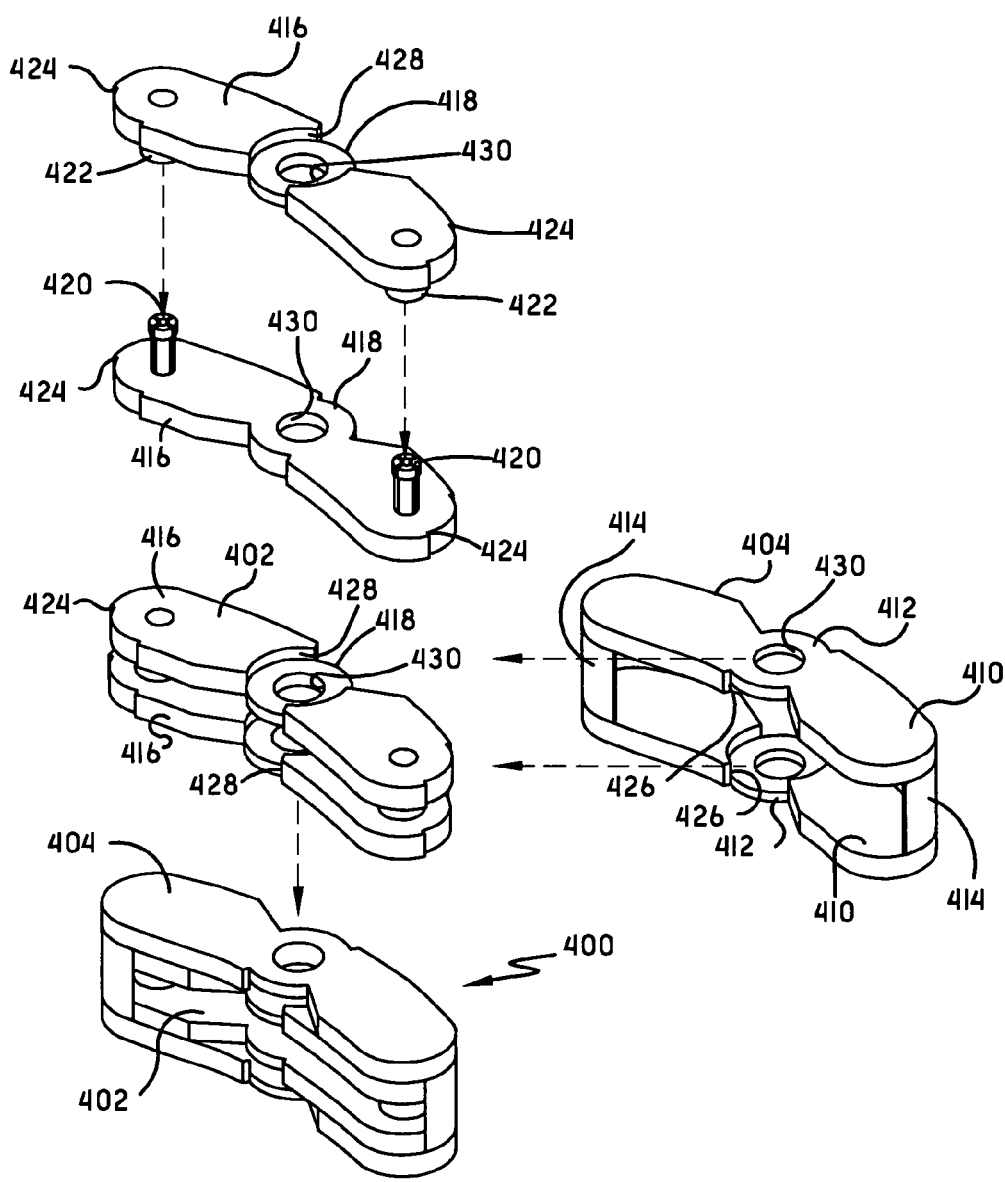
FIG. 17 is an assembly drawing of the implant embodiment shown in FIGS. 16a, 16b and 16c.
Figure 18:
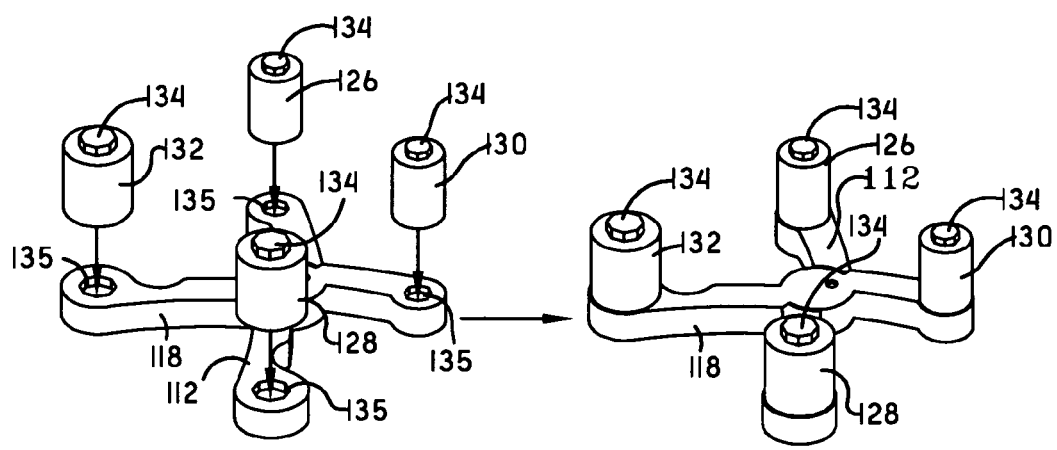
FIG. 18 is an assembly drawing illustrating one embodiment of how the posts may attach to the beams.

Still referring to FIGS. 16a, 16b, 16c and 17, to deploy the implant 400 from the non-deployed condition, shown in FIG. 16a, the first member 402 is pivoted with respect to the second member 404, as shown in FIG. 16b. As noted above, the posts 420 may be spring loaded to urge the beams 416, 416 away from each other. The beams 416, 416, however, cannot yet achieve their fully expanded condition. As the first member 402 continues to be pivoted with respect to the second member 404, the notches 426 in the beams 410 align with the notches 428 in the beams 416. With this alignment the posts 420 extend fully within the receiving members 422 and the beams 416, 416 achieve their fully expanded condition. This also means that the implant 400 is thus placed into the fully deployed condition, as shown in FIG. 16c.

Figure 8:
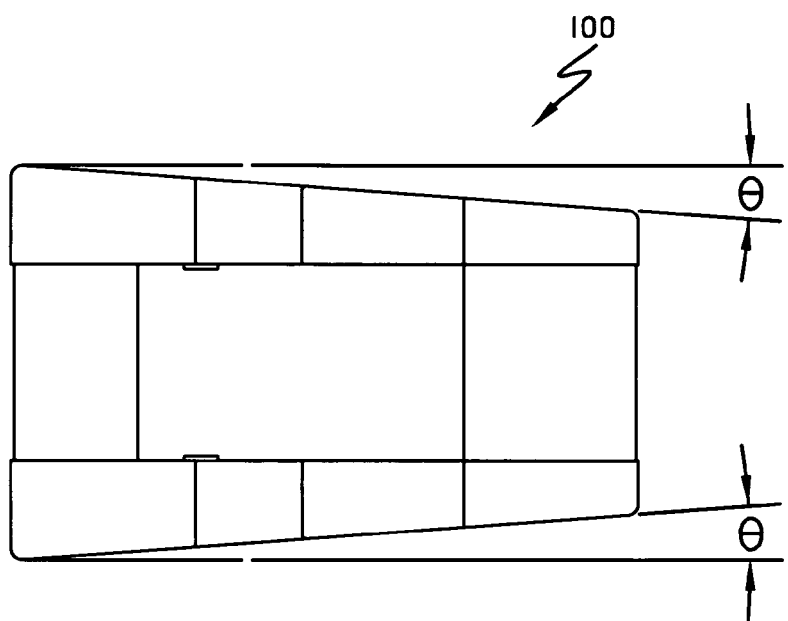
FIG. 8 is a side view of an alternate embodiment showing lordotic taper.

With reference now to FIG. 8, another embodiment is shown. In this case, the embodiment is very similar to and operates in the same manner as the implant 100 described above. In this case, however, the implant 100 is tapered to allow for lordotic taper. In the lordotic taper mode, the height of the implant 100 would be greater in quadrants I and II than in quadrants III and IV, with the height tapering gradually at angle theta from front to back, as shown. This lordotic taper mimics the natural lordotic taper of most vertebral spaces from anterior to posterior (front to back). Of course other tapering angles and shapes are possible with this invention.

While the embodiments disclosed include the pivoting motion of one member with respect to another member to achieve the expanded condition and thus the increased effective footprint, it is noted that other devices and corresponding methods of expanding the endplate footprint of an implant are also contemplated. Once such device, for example, is an implant that can be inflated to achieve the expanded footprint. It should also be noted that while the implant embodiments provided are all of the "scissor" movement type, other shapes and forms of movement could work equally well with this invention.

In the illustrated embodiments described so far, the focus has been on a minimally invasive, deployable, expandable interbody fusion device. However, it is understood that the present invention has utility in implanting other types of devices including, but not limited to, threaded, non-threaded fusion devices, threaded and non-threaded spacers, and cylindrical, or non-cylindrical devices, disc replacement devices, and osteobiologic material.

In another embodiment, the implant may provide at least some amount of motion preservation for the spine segment, either constrained or unconstrained. If the motion preservation provided is similar to that provided by a healthy spine segment (whether just a single disc or any combination of discs and vertebrae) then the implant may be thought of as an artificial spine segment (an artificial disc if only one disc is replaced with the implant). Motion preservation may provide for the possibility of load-sharing between the implant and the host bone of the adjacent vertebrae. Motion preservation may also enhance bonegraft consolidation and/or healing. The inventors contemplate multiple embodiments for achieving the motion preservation for the implant. In one embodiment, relative motion of one portion of the implant with respect to another portion of the implant is used. In one specific embodiment, motion between the top and bottom beams is permitted.

Figure 24:
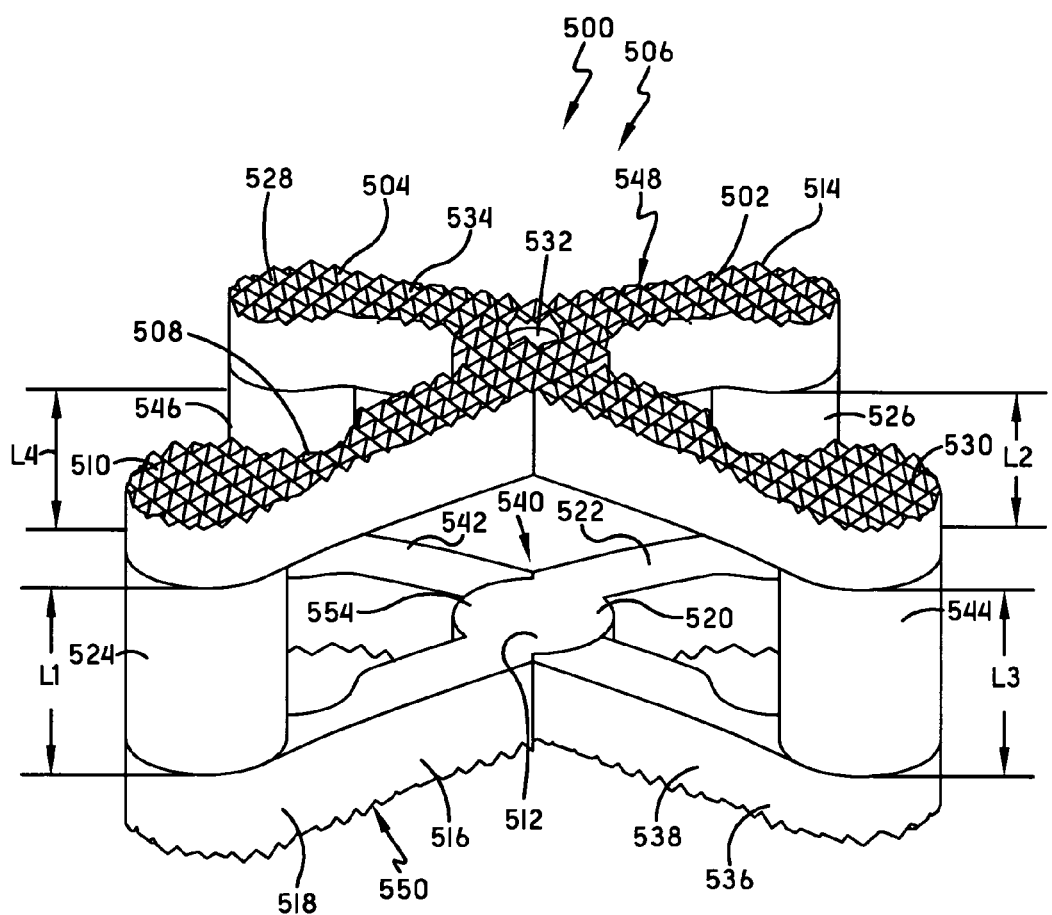
FIG. 24 is a perspective side view of another implant embodiment shown in the expanded, deployed condition.

With reference now to FIG. 24, in one embodiment, an implant 500 may be similar to the implant 100 described above except that implant 500 provides motion preservation as will be described further below. The implant 500 may have a first member 502, a second member 504 and a pivoting connection 506 between the first and second members 502, 504 permitting the second member 504 to pivot with respect to the first member 502 from a first non-expanded condition (not shown but similar to that shown in FIG. 2) to a second expanded condition, shown in FIG. 24. The first member 502 may include a first beam 508 having a first limb 510, a mid-portion 512, and a second limb 514 as well as a second beam 516 having a first limb 518, a mid-portion 520, and a second limb 522. A first post 524 may have a first end operatively connected to the first limb 510 of the first beam 508 and a second end operatively connected to the first limb 518 of the second beam 516. A second post 526 may have a first end operatively connected to the second limb 514 of the first beam 508 and a second end operatively connected to the second limb 522 of the second beam 516. The first and second posts 524, 526 may each have a length, L1, L2 respectively, defined as the distance between their first and second ends.

With continuing reference to FIG. 24, the second member 504 may include a first beam 528 having a first limb 530, a mid-portion 532, and a second limb 534 as well as a second beam 536 having a first limb 538, a mid-portion 540, and a second limb 542. A third post 544 may have a first end operatively connected to the first limb 530 of the first beam 528 and a second end operatively connected to the first limb 538 of the second beam 536. A fourth post 546 may have a first end operatively connected to the second limb 534 of the first beam 528 and a second end operatively connected to the second limb 542 of the second beam 536. The third and fourth posts 544, 546 may each have a length L3, L4 respectively, defined as the distance between their first and second ends. The outer surfaces of the beams may define first and second contact surfaces 548, 550 that may be serrated/knurled as shown. The posts 524, 526, 544, 546 may attach to the corresponding beams in any manner chosen with the sound judgment of a person of skill in the art.

Still referring to FIG. 24, in one embodiment, the pivoting connection 506 may include a first pivotal connection 552 defined by the pivotal engagement of the mid-portion 512 of the first beam 508 of the first member 502 with the mid-portion 532 of the first beam 528 of the second member 504. The pivoting connection 506 may also include a second pivotal connection 554 defined by the pivotal engagement of the mid-portion 520 of the second beam 516 of the first member 502 with the mid-portion 540 of the second beam 536 of the second member 504.

Figure 25:
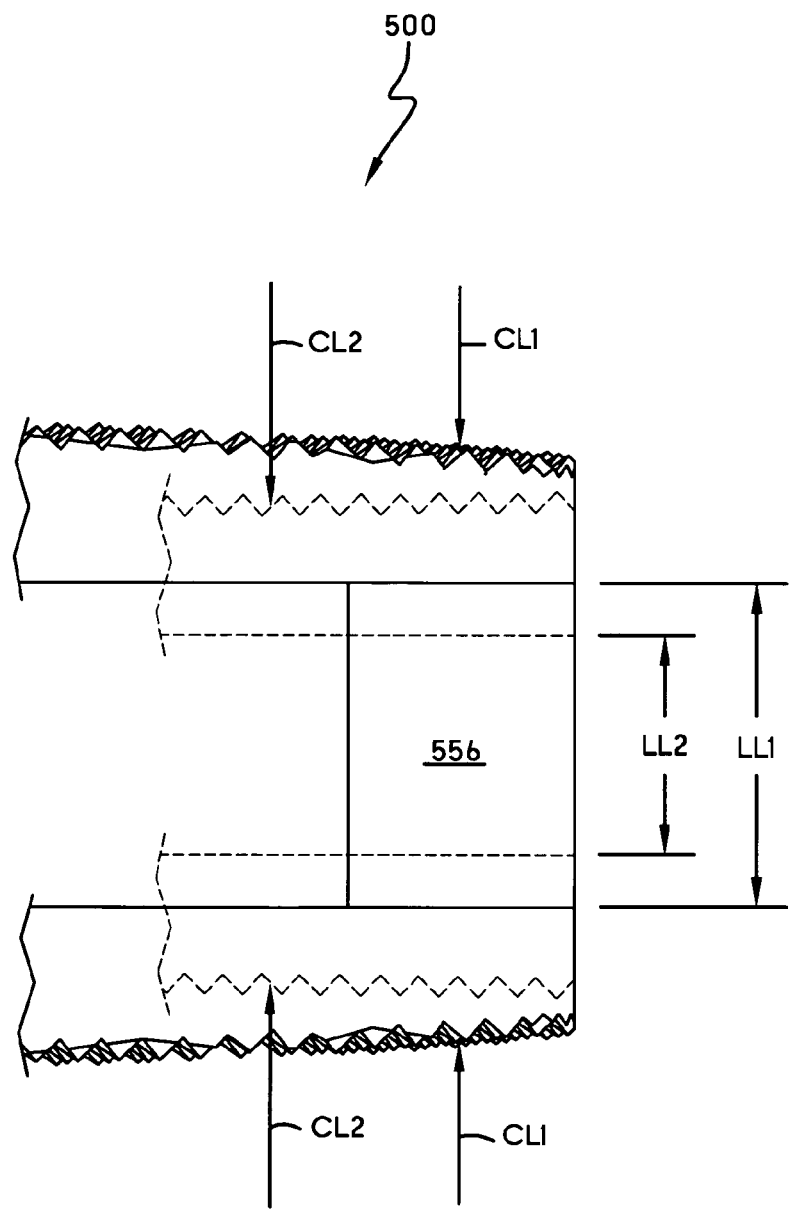
FIG. 25 is a close-up side view of a portion of an implant showing how a post may length vary under a compression load.

With reference now to FIGS. 24 and 25, to achieve motion preservation, one or more of the posts 524, 526, 544, 546, may be length variable in response to a load put on the implant 500 by the vertebral bodies after deployment of the implant 500. By "length variable" it is meant that the length of the post will change in reaction to a load put on the post. In one embodiment, the post length changes by decreasing in length in response to a compression load put on the implant. FIG. 25, for example, shows a post 556 (which could be any post positioned between implant beams, including any number of the posts 524, 526, 544, 546,) having a length LL1 when the implant 500 has no compression load (in other words, compression load CL1 is 0). FIG. 25 also shows the same post 556 (in dashed lines) under a compression load (in other words, compression load CL2 is greater than 0) having a reduced or decreased length LL2 that is less than length LL1.

Figure 26:
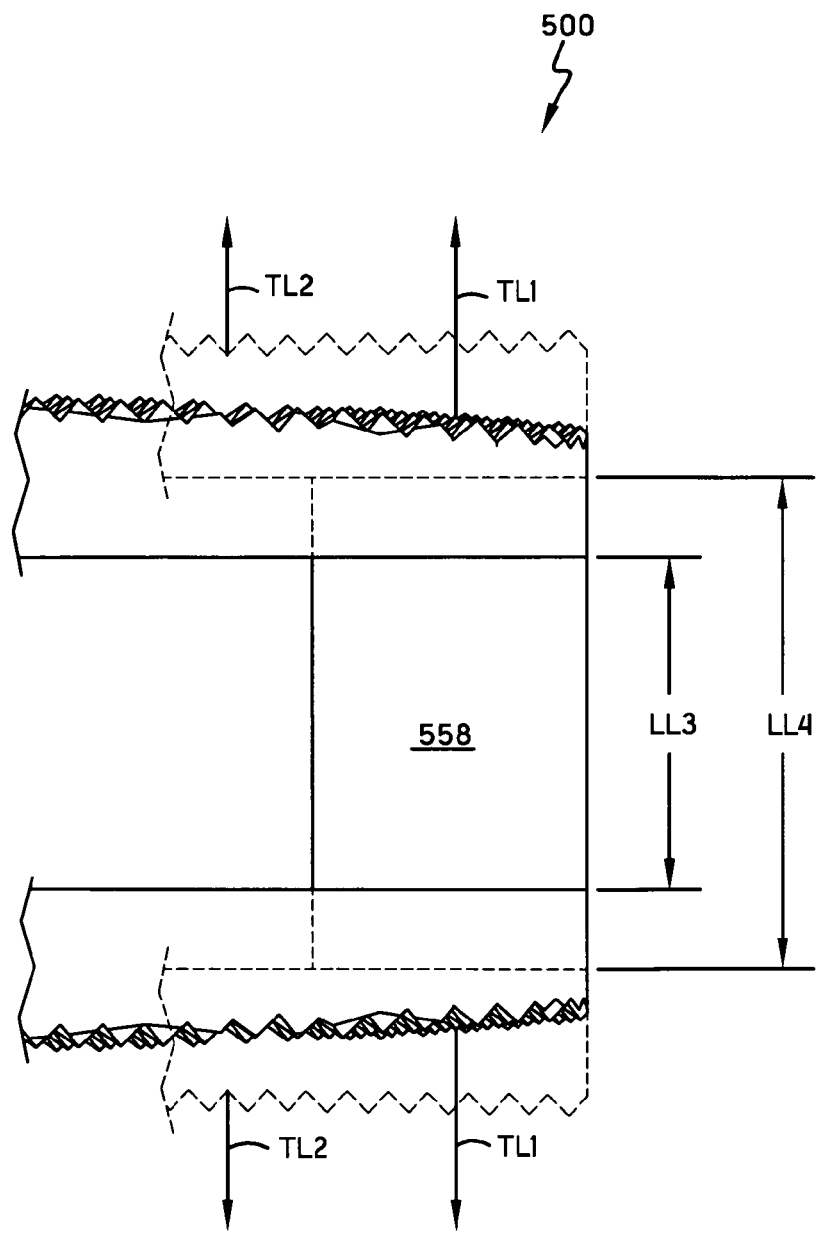
FIG. 26 is a close-up side view of a portion of an implant showing how a post may length vary under a tension load.

With reference now to FIGS. 24 and 26, to achieve motion preservation in another embodiment, the post length changes by increasing in length in response to a tension load put on the implant. FIG. 26, for example, shows a post 558 (which could be any post positioned between implant beams, including any number of the posts 524, 526, 544, 546,) having a length LL3 when the implant 500 has no tension load (in other words, tension load TL1 is 0). FIG. 26 also shows the same post 558 (in dashed lines) under a tension load (in other words, tension load TL2 is greater than 0) having an increased length LL4 that is greater than length LL1.

Figure 27:
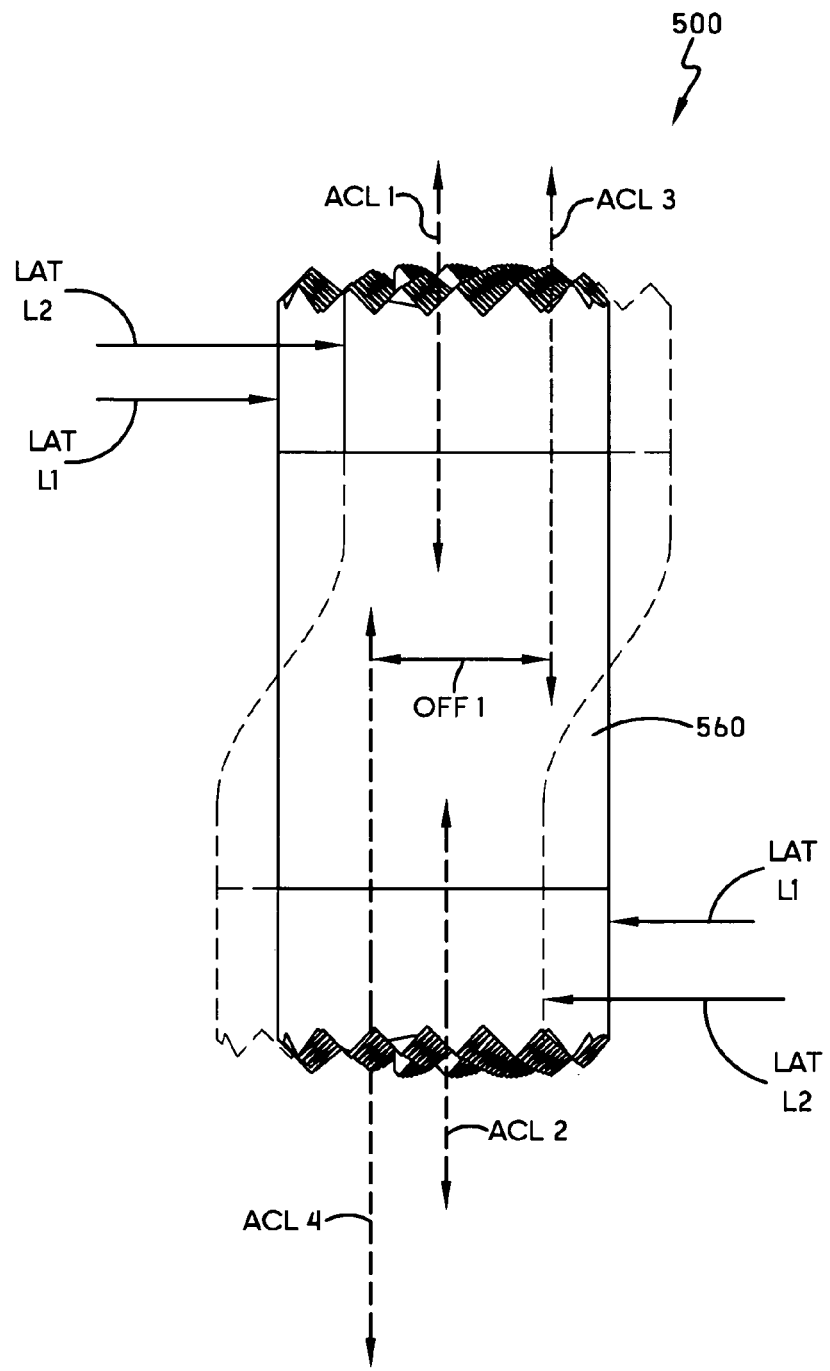
FIG. 27 is a close-up side view of a portion of an implant showing how a post may laterally vary under a lateral load.

With reference now to FIGS. 24 and 27, in yet another embodiment to achieve motion preservation, one or more of the posts 524, 526, 544, 546, may be laterally variable in response to a load put on the implant 500 by the vertebral bodies after deployment of the implant 500. By "laterally variable" it is meant that the axial center line of one end of the post will become non-collinear with the axial center line of the opposite end of the post due to a lateral or shear load put on the post. FIG. 27, for example, shows a post 560 (which could be any post positioned between implant beams, including any number of the posts 524, 526, 544, 546,) having a first axial centerline ACL1 at the top end of the post 560 and having a second axial centerline ACL2 at the bottom end of the post 560 when the implant 500 has no lateral load (in other words, lateral load LATL1 is 0). Note that with no lateral load, the first axial centerline ACL1 and the second axial centerline ACL2 are collinear. FIG. 27 also shows the same post 560 (in dashed lines) under a lateral load (in other words, lateral load LATL2 is greater than 0) where the first axial centerline ACL3 and the second axial centerline ACL4 are not collinear but are offset an amount OFF1.

Figure 28:
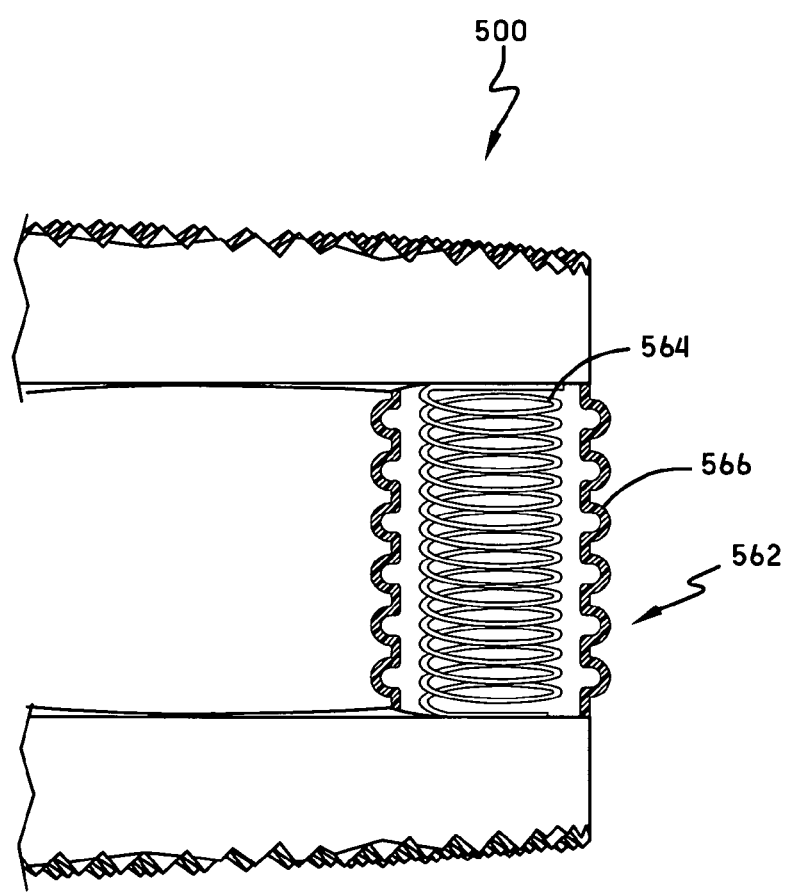
FIG. 28 is a close-up side view of a portion of an implant showing a post comprising a spring according to one embodiment of this invention.

With reference again to FIG. 24, in one embodiment, the post (or posts) which achieve the motion preservation is formed, at least partially, of any viscoelastic material chosen with the sound judgment of a person of skill in the art. By "viscoelastic material," it is meant any material that provides both viscous and elastic properties. By "at least partially of any viscoelastic material" it is meant that either the entire post or any portion of the post may be formed of a viscoelastic material to achieve the motion preservation. Thus a hybrid post formed in part of a viscoelastic material and in part of any other material or materials is here contemplated. The use of posts formed at least partially of viscoelastic material may provide: (1) length variation under compression (illustrated in FIG. 25); (2) length variation under tension (illustrated in FIG. 26); and, (3) lateral variation (illustrated in FIG. 27), as understood by those of skill in the art. In another embodiment, illustrated in FIG. 28, motion preservation may be achieved by providing the implant 500 with one or more posts 562 formed of at least one spring 564 having a spring constant chosen to match the desired flexibility required. The post 562 may be used to provide: (1) length variation under compression (illustrated in FIG. 25); and/or (2) length variation under tension (illustrated in FIG. 26); and/or, (3) lateral variation (illustrated in FIG. 27), as understood by those of skill in the art. In order to protect the spring 564, a spring cover or shield 566 may be used. The spring cover 566 may be formed of any material chosen with the sound judgment of person of skill in the art such as a viscoelastic material. In another embodiment, shown, the spring cover 566 may be an expandable, contactable bellows.

Figure 29:
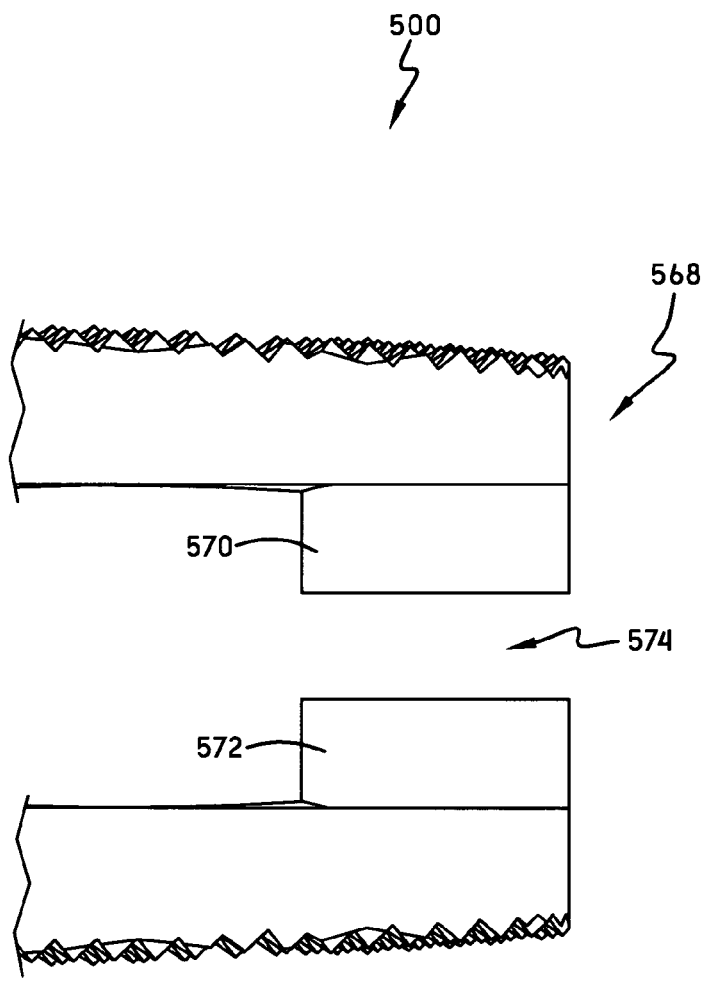
FIG. 29 is a close-up side view of a portion of an implant showing a post comprising first and second portions separated by a space according to another embodiment of this invention.

With reference now to FIGS. 24 and 29, in another embodiment motion preservation may be achieved by permitting relative motion of one portion of the post with respect to another portion of the post. In one specific embodiment, shown in FIG. 29, the implant 500 uses at least one post 568 having first and second portions 570, 572 separated by a space 574. The space 574 may be provided with any device and/or material chosen with the sound judgment of person of skill in the art to provide relative motion of the first portion 570 with respect to the second portion 572. In one embodiment, a viscoelastic material is placed into the space 574. In another embodiment, a spring (not shown but similar to that shown in FIG. 28 but of a reduced longitudinal size) may be placed into the space 574. In yet another embodiment, a bladder (not shown but similar to that shown in FIG. 31 but of a reduced size) may be placed into the space 574. The bladder may be prefilled with a compressible fluid and/or may be inflatable or fillable (before or after insertion within the vertebral space) with a compressible fluid. In another embodiment, the bladder may contain a viscoelastic substance instead of (or in addition to) a compressible fluid. The post 568 may be used to provide: (1) length variation under compression (similar to that illustrated in FIG. 25) as when first portion 570 and second portion 572 move relatively toward each other; and/or (2) length variation under tension (similar to that illustrated in FIG. 26) as when first portion 570 and second portion 572 move relatively away from each other; and/or, (3) lateral variation (similar to that illustrated in FIG. 27) as when first portion 570 moves in one lateral direction and second portion 572 moves in another lateral direction, as understood by those of skill in the art.

Figure 30:
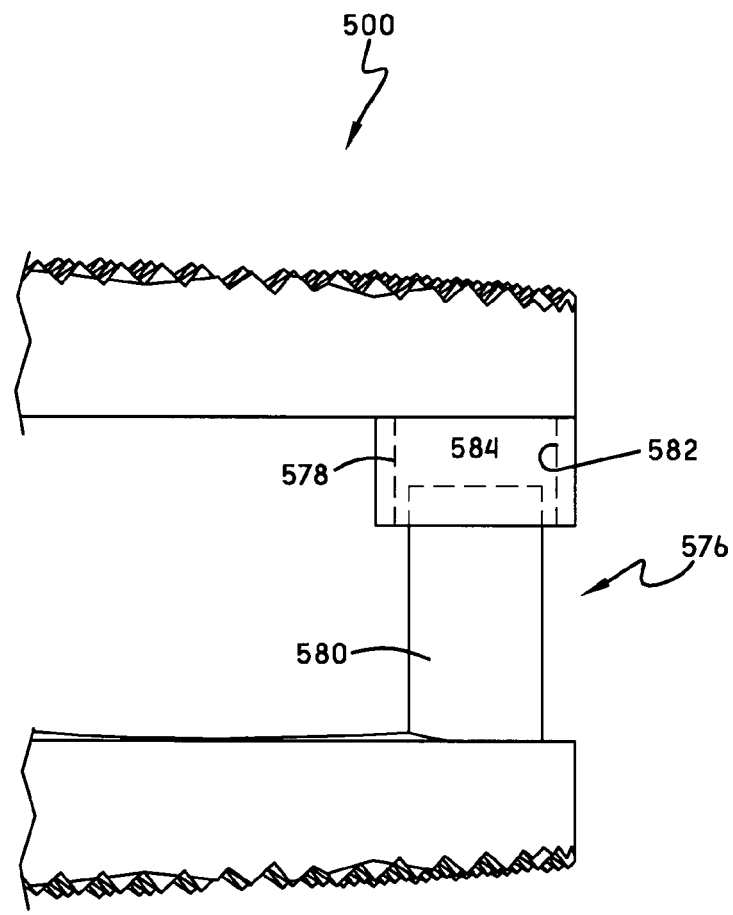
FIG. 30 is a close-up side view of a portion of an implant showing a post comprising first and second portions where one portion has a cavity that receives at least a part of the second portion according to another embodiment of this invention.

With reference now to FIGS. 24 and 30, in another embodiment motion preservation may be achieved by permitting relative motion of one portion of the post with respect to another portion of the post where at least a part of one of the two portions is received within at least a part of the other portion. In one specific embodiment, shown in FIG. 30, the implant 500 uses at least one post 576 having first and second portions 578, 580. The first portion 578 may have a cavity 582 that receives a portion of the second portion 580, as shown. Within the cavity 582, a space 584 is provided between the distal end of the second portion 580 and the proximal end of the cavity 582. The space 584 may be provided with any device and/or material chosen with the sound judgment of person of skill in the art to provide relative motion of the first portion 578 with respect to the second portion 580. In one embodiment, a viscoelastic material is placed into the space 584. In another embodiment, a spring (not shown but similar to that shown in FIG. 28 but of a reduced longitudinal size) may be placed into the space 584. In yet another embodiment, a bladder (not shown but similar to that shown in FIG. 31 but of a reduced size) may be placed into the space 584. The bladder may be prefilled with a compressible fluid and/or may be inflatable or fillable (before or after insertion within the vertebral space) with a compressible fluid. The post 576 may be used to provide: (1) length variation under compression (similar to that illustrated in FIG. 25) as when the distal end of the second member 580 moves within the space 584 toward the proximal end of the cavity 582; and/or (2) length variation under tension (similar to that illustrated in FIG. 26) as when the distal end of the second member 580 moves within the space 584 away from the proximal end of the cavity 582; and/or, (3) lateral variation (similar to that illustrated in FIG. 27) as when first portion 578 moves in one lateral direction and second portion 580 moves in another lateral direction, as understood by those of skill in the art. The amount of lateral variation can be predetermined by controlling the space between the outer surface of the distal end of the second portion 580 and the inner surface of the first portion 578 forming the outer surface of the cavity 582. If this space is minimal, providing a relatively tight fit between the distal end of the second member 580 and the inner surface of the first portion 578, the lateral variation can be reduced to essentially zero.

Figure 31:
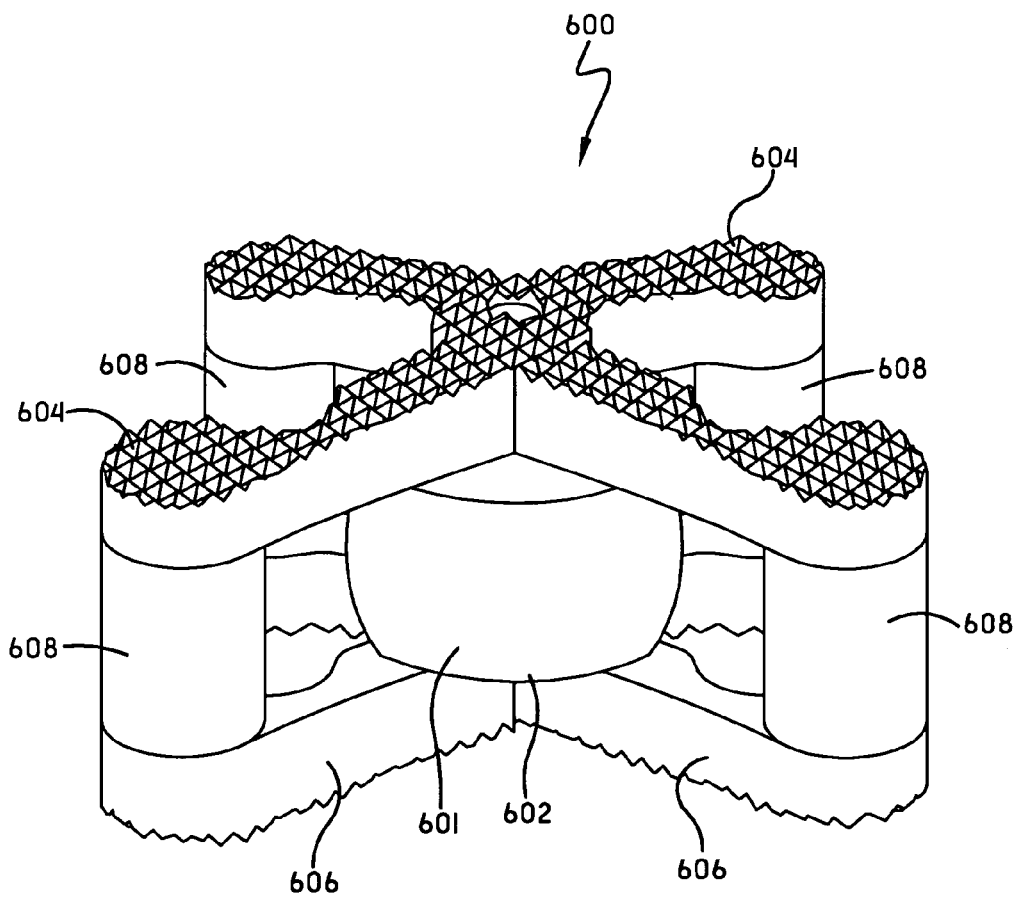
FIG. 31 is a perspective side view of another implant embodiment shown in the expanded, deployed condition and using a centrally positioned bladder.

With reference now to FIGS. 1A, 1B and 31, in another embodiment motion preservation may include the use of a bladder 602 positioned at or near the center of the implant 600. As shown, the bladder 602 may be positioned vertically between the upper and lower beams 604, 606, respectively and horizontally between the posts 608, juxtaposed to the pivotal connections. In one embodiment, the bladder 602 may be attached to the undersides of the upper and lower beams 604, 606 prior to surgery and thus the bladder 602 may be positioned within the vertebral space 22 along with the implant 600. In another embodiment, the bladder 602 may be positioned into the implant 600 after the implant 600 has been inserted and deployed within the vertebral space 22. The bladder 602 may be prefilled with a compressible fluid and/or may be inflatable or fillable (before or after insertion within the vertebral space) with a compressible fluid. In another embodiment, the bladder may contain a viscoelastic substance instead of (or in addition to) a compressible fluid. The bladder 602 may have an outer surface 610 that defines an inner cavity that receives the compressible fluid and/or the viscoelastic substance. The outer surface 610 may be formed of a viscoelastic substance to permit the implant 600 to move. It should be noted that the lateral area of the implant 600 over which motion preservation is provided can be predetermined.

If, for example, the posts 608 are vertically rigid, as with posts 126, 128, 130 and 132 as shown in FIGS. 2-4, then the vertical motion of the implant 600 will be restricted to the central portion of the implant 600 at the location of the bladder 602. In another embodiment, if the posts 608 permit motion as the posts 556, 558, 562, 568, and/or 576 (shown in FIGS. 25-30) then the vertical motion of the implant 600 will be possible all across the lateral area of the implant. Note that vertical motion of the implant 600 can also be predetermined by the use of specific posts, as described above.

Figure 32:
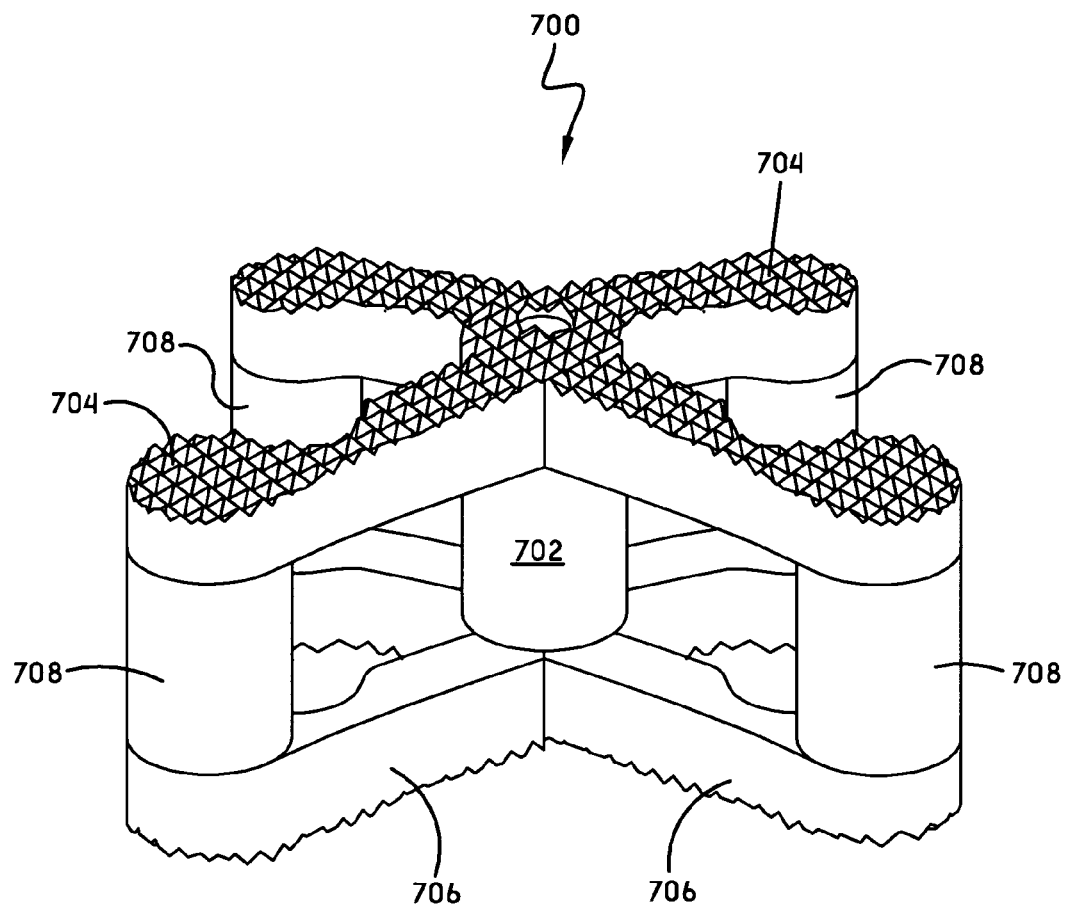
FIG. 32 is a perspective side view of another implant embodiment shown in the expanded, deployed condition and using a centrally positioned post.

With reference now to FIGS. 1A, 1B and 32, in another embodiment an inner post 702 may be positioned at or near the center of the implant 700. As shown, the post 702 may be positioned vertically between the upper and lower beams 704, 706, respectively and horizontally between the outer posts 708, juxtaposed to the pivotal connections. In one embodiment, the post 702 may be attached to the undersides of the upper and lower beams 704, 706 prior to surgery and thus the post 702 may be positioned within the vertebral space 22 along with the implant 700. In another embodiment, the post 702 may be positioned into the implant 700 after the implant 700 has been inserted and deployed within the vertebral space 22. It should be noted that the lateral area of the implant 700 over which motion preservation is provided can be predetermined. In one embodiment the inner post 702 and the outer posts 708 are vertically rigid, as with posts 126, 128, 130 and 132 as shown in FIGS. 2-4. In this case the implant 700 will not permit any motion for the joint segment. In another embodiment, the inner post 702 permits motion as the posts 556, 558, 562, 568, and/or 576 (shown in FIGS. 25-30) while the outer posts 708 are vertically rigid, as with posts 126, 128, 130 and 132 as shown in FIGS. 2-4. In this case, vertical motion of the implant 700 will be restricted to the central portion of the implant 700 at the location of the inner post 702. In yet another embodiment, the inner post 702 is vertically rigid, as with posts 126, 128, 130 and 132 as shown in FIGS. 2-4 while the outer posts 708 permit motion as the posts 556, 558, 562, 568, and/or 576 (shown in FIGS. 25-30). In this case, vertical motion of the implant 700 will be restricted at the central portion of the implant 700 but will be permitted at the outer surfaces at the location of the outer posts 708.

Figure 33:
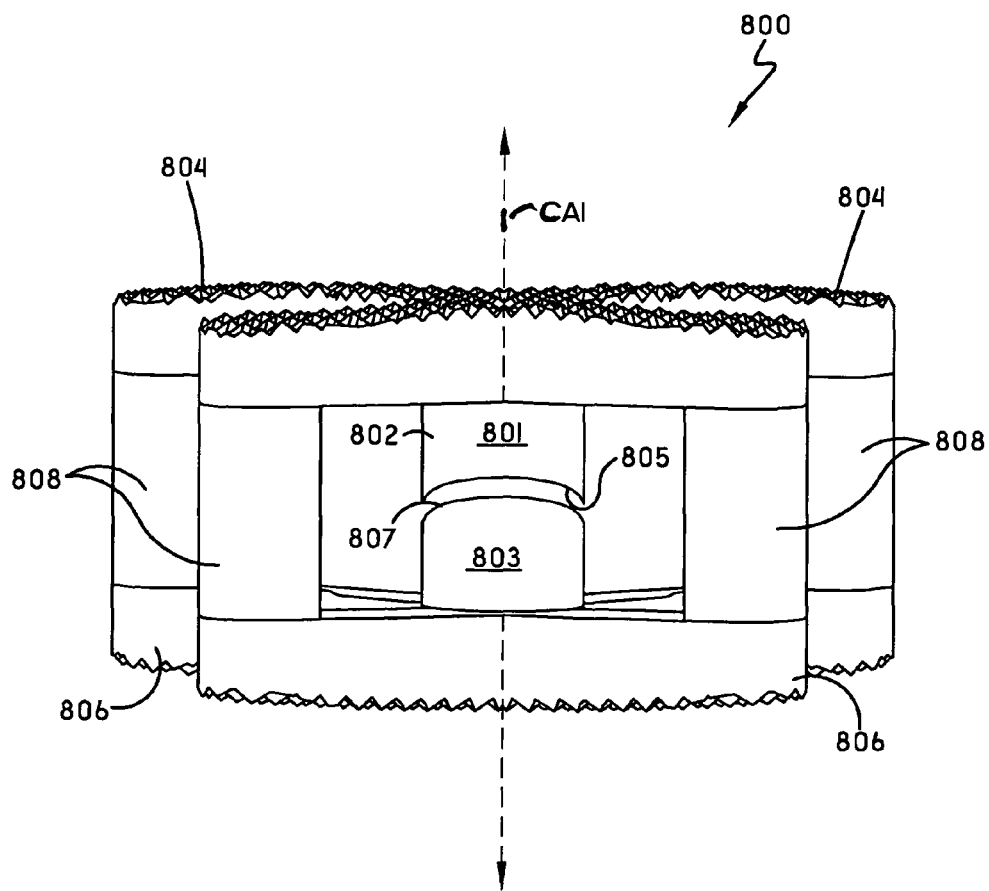
FIG. 33 is a perspective side view of another implant embodiment shown in the expanded, deployed condition and using a centrally positioned post that has a first portion with a convex surface that is received in a concave surface formed on a second portion.

With reference now to FIGS. 1A, 1B and 33, in another embodiment an inner post 802 may be positioned at or near the center of the implant 800. This implant 800 is similar to the implant 700 shown in FIG. 32 except for the design of the inner post 802. The post 802 has a first portion 801 and a second portion 803. The distal end of the first portion 801 has a surface 805 with a concave shape that receives the surface 807, having a convex shape, of the distal end of the second portion 803. In this way the inner post 802 defines a pivotal central axis CA1 for the implant 800. In one embodiment, the outer posts 808 permit motion as the posts 556, 558, 562, 568, and/or 586 (shown in FIGS. 25-30). In this case, vertical and/or lateral motion of the implant 800 is possible as the outer posts 808 flex under load while the first portion 801 of the inner post 802 moves (pivots) with respect to the second portion 803 at the intersection of the surfaces 805 and 807. Note that while in the embodiment shown the surface 807 is a semispherical convex surface that matches and engages the semispherical concave surface 805, these surfaces can be of any shape chosen with the sound judgment of a person of skill in the art.

With reference now to FIGS. 24-33, it should be noted that the motion preservation embodiments provide for posts that work independently of each other allowing for complex motion of the implant as a whole. Some non-limiting motions available include flexion, extension in the anteroposterior plane and lateral flexion and extension as would take place in the normal motion of a lumbar spine segment. In embodiments where an inter post is used, the inner post may be used as a major load bearing member and allow selective loading of the outer posts in either tensile or compression modes depending on the external load on the spine segment. Any number of posts may be used when chosen with the sound judgment of a person of skill in the art and the posts may be individually constructed as required for a particular use. Thus, for example, one or more posts may be vertically rigid, while one or more other posts permit motion. As another example, one post may permit a certain degree or amount of motion while another post on the same implant permits a different degree or amount of motion. This may be accomplished by using variations of the embodiments described above. One post may be formed similar to that shown in FIG. 30, for example, while other posts on the same implant may be formed similar to that shown in FIG. 27, 28 and/or 29. As another example, one post may be formed of a first viscoelastic material providing a first set of motion characteristics while one or more other posts on the same implant may be formed of a second viscoelastic material providing a second set of motion characteristics.

With reference to all the FIGURES, all the implant embodiments may be formed of any material that is appropriate for insertion into an vertebral space, including, but not limited to metal, metal alloy, titanium, titanium alloy, ceramic, carbon-fiber, PEEK or any other osteobiologic or inert, biocompatible material.

Multiple embodiments have been described, hereinabove. It will be apparent to those skilled in the art that the above apparatuses and methods may incorporate changes and modifications without departing from the general scope of this invention. It is intended to include all such modifications and alterations in so far as they come within the scope of the appended claims or the equivalents thereof.

I claim:
1. An implant comprising:
 a first member comprising:
  (1) a first beam having a first limb, a mid-portion, and a second limb;
  (2) a second beam having a first limb, a mid-portion, and a second limb;
  (3) a first post having a first end operatively connected to the first limb of the first beam and a second end operatively connected to the first limb of the second beam, the first post having a length defined as the distance between its first and second ends; and,
  (4) a second post having a first end operatively connected to the second limb of the first beam and a second end operatively connected to the second limb of the second beam, the second post having a length defined as the distance between its first and second ends;
 a second member that is pivotal with respect to the first member, comprising:
  (1) a first beam having a first limb, a mid-portion, and a second limb;
  (2) a second beam having a first limb, a mid-portion, and a second limb;
  (3) a third post having a first end operatively connected to the first limb of the first beam and a second end operatively connected to the first limb of the second beam, the third post having a length defined as the distance between its first and second ends; and,
  (4) a fourth post having a first end operatively connected to the second limb of the first beam and a second end operatively connected to the second limb of the second beam, the fourth post having a length defined as the distance between its first and second ends;

wherein the first beam of the first member and the first beam of the second member define a first contact surface that contacts the endplate of a first vertebral body;

wherein the second beam of the first member and the second beam of the second member define a second contact surface that contacts the endplate of a second vertebral body;

wherein the implant is deployable, when positioned within a vertebral space between the first and second vertebral bodies, from a first non-expanded condition where the first contact surface has a first effective footprint area A1 to a second expanded condition where the first contact surface has a second effective footprint area A2, the ratio A2/A1 is at least 1.05; and, wherein the first, second, third and fourth posts are length variable in response to a load put on the implant by the first and second vertebral bodies after deployment of the implant.

2. The implant of claim 1 wherein the first, second, third and fourth posts are laterally variable in response to a lateral load put on the implant by the first and second associated vertebral bodies after deployment of the implant.

3. The implant of claim 2 wherein the first, second, third and fourth posts are formed, at least partially, of a viscoelastic material that provides the length and lateral variability.

4. The implant of claim 1 wherein the first, second, third and fourth posts each comprise a spring.

5. The implant of claim 1 further wherein:
the mid-portion of the first beam of the first member and the mid-portion of the first beam of the second member are pivotally connected and define a first pivotal connection;
the mid-portion of the second beam of the first member and the mid-portion of the second beam of the second member are pivotally connected and define a second pivotal connection; and,
the implant further comprises: a bladder formed of a viscoelastic material that supports the first pivotal connection to the second pivotal connection.

6. The implant of claim 5 wherein the bladder is inflatable.

7. The implant of claim 1 further wherein:
the mid-portion of the first beam of the first member and the mid-portion of the first beam of the second member are pivotally connected and define a first pivotal connection;
the mid-portion of the second beam of the first member and the mid-portion of the second beam of the second member are pivotally connected and define a second pivotal connection; and,
the implant further comprises: a fifth post having a first end operatively connected to the first pivotal connection and a second end operatively connected to the second pivotal connection.

8. The implant of claim 7 wherein the fifth post comprises:
a first portion having a proximal end defining the first end of the fifth post and a distal end having a concave surface;
a second portion having a proximal end defining the second end of the fifth post and a distal end having a convex surface that engages the concave surface; and,
wherein the engagement of the concave surface with the convex surface permits the first portion to pivot with respect to the second portion in response to a load put on the implant by the first and second vertebral bodies after deployment of the implant.

9. The implant of claim 7 wherein the fifth post has a longitudinal axis that is substantially collinear with the center axis of the implant.

10. The implant of claim 7 wherein the fifth post is length variable in response to a load put on the implant by the first and second vertebral bodies after deployment of the implant.

11. An implant comprising:
a first member comprising:
(1) a first beam having a first limb, a mid-portion, and a second limb;
(2) a second beam having a first limb, a mid-portion, and a second limb;
(3) a first post having a first end operatively connected to the first limb of the first beam and a second end operatively connected to the first limb of the second beam, the first post having a length defined as the distance between its first and second ends; and,
(4) a second post having a first end operatively connected to the second limb of the first beam and a second end operatively connected to the second limb of the second beam, the second post having a length defined as the distance between its first and second ends;
a second member that is pivotal with respect to the first member, comprising:
(1) a first beam having a first limb, a mid-portion, and a second limb;
(2) a second beam having a first limb, a mid-portion, and a second limb;
(3) a third post having a first end operatively connected to the first limb of the first beam and a second end operatively connected to the first limb of the second beam, the third post having a length defined as the distance between its first and second ends; and,
(4) a fourth post having a first end operatively connected to the second limb of the first beam and a second end operatively connected to the second limb of the second beam, the fourth post having a length defined as the distance between its first and second ends;
wherein the first beam of the first member and the first beam of the second member define a first contact surface that contacts the endplate of a first associated vertebral body;
wherein the second beam of the first member and the second beam of the second member define a second contact surface that contacts the endplate of a second associated vertebral body;
wherein the implant is deployable, when positioned within a vertebral space between the first and second vertebral bodies, from a first non-expanded condition where the first contact surface has a first effective footprint area A1 to a second expanded condition where the first contact surface has a second effective footprint area A2, the ratio A2/A1 is at least 1.05; and,
wherein at least one of the first, second, third and fourth posts is length variable in response to a load put on the implant by the first and second associated vertebral bodies after deployment of the implant.

12. The implant of claim 1 wherein at least two of the first, second, third and fourth posts are length variable in response to the load put on the implant by the first and second vertebral bodies after deployment of the implant.

13. The implant of claim 12 where one of the posts that is length variable is formed of a first viscoelastic material providing a first motion characteristic and the other of the posts that is length variable is formed of a second viscoelastic material providing a second motion characteristic that is substantially different than the first motion characteristic.

14. The implant of claim 11 wherein the post that is length variable decreases in length in response to a compression load put on the implant by the first and second vertebral bodies after deployment of the implant.

15. The implant of claim 11 wherein the post that is length variable increases in length in response to a tensile load put on the implant by the first and second vertebral bodies after deployment of the implant.

16. The implant of claim 11 wherein the post that is length variable is formed of a viscoelastic material.

17. The implant of claim 11 wherein the post that is length variable is also laterally variable in response to a lateral load put on the implant by the first and second associated vertebral bodies after deployment of the implant.

18. The implant of claim 11 wherein the post that is length variable comprises a spring that is used to provide the length variation.

19. The implant of claim 11 wherein:
the post that is length variable comprises first and second portions separated by a space;
the first and second portions move relative to each other as the post that is length variable varies in length; and,
at least one spring that is used to provide the length variation is positioned within the space.

20. The implant of claim 11 wherein:
the post that is length variable comprises first and second portions separated by a space;
the first and second portions move relative to each other as the post that is length variable varies in length; and,
a viscoelastic material that is used to provide the length variation is positioned within the space.

21. The implant of claim 11 wherein:
the post that is length variable comprises first and second portions separated by a space;
the first and second portions move relative to each other as the post that is length variable varies in length; and,
a bladder that receives a compressible fluid and that is used to provide the length variation is positioned within the space.

22. The implant of claim 11 wherein:
the post that is length variable comprises first and second portions;
the first portion comprises a cavity; and,
at least a part of the second portions moves within the cavity as the post that is length variable varies in length.

23. The implant of claim 11 wherein:
the mid-portion of the first beam of the first member and the mid-portion of the first beam of the second member are pivotally connected and define a first pivotal connection;
the mid-portion of the second beam of the first member and the mid-portion of the second beam of the second member are pivotally connected and define a second pivotal connection; and,
the implant further comprises: a fifth post having a first end operatively connected to the first pivotal connection and a second end operatively connected to the second pivotal connection.

24. The implant of claim 23 wherein the fifth post comprises:
a first portion having a proximal end defining the first end of the fifth post and a distal end having a concave surface;
a second portion having a proximal end defining the second end of the fifth post and a distal end having a convex surface that engages the concave surface; and,
wherein the engagement of the concave surface with the convex surface permits the first portion to pivot with respect to the second portion in response to a load put on the implant by the first and second vertebral bodies after deployment of the implant.

25. The implant of claim 23 wherein the fifth post has a longitudinal axis that is substantially collinear with the center axis of the implant.

26. The implant of claim 23 wherein the fifth post is length variable in response to a load put on the implant by the first and second vertebral bodies after deployment of the implant.

27. An implant comprising:
a first member comprising:
(1) a first beam having a first limb, a mid-portion, and a second limb;
(2) a second beam having a first limb, a mid-portion, and a second limb;
(3) a first post having a first end operatively connected to the first limb of the first beam and a second end operatively connected to the first limb of the second beam; and,
(4) a second post having a first end operatively connected to the second limb of the first beam and a second end operatively connected to the second limb of the second beam;
a second member that is pivotal with respect to the first member, comprising:
(1) a first beam having a first limb, a mid-portion, and a second limb;
(2) a second beam having a first limb, a mid-portion, and a second limb;
(3) a third post having a first end operatively connected to the first limb of the first beam and a second end operatively connected to the first limb of the second beam; and,
(4) a fourth post having a first end operatively connected to the second limb of the first beam and a second end operatively connected to the second limb of the second beam;
wherein the first beam of the first member and the first beam of the second member define a first contact surface that contacts the endplate of a first associated vertebral body;
wherein the second beam of the first member and the second beam of the second member define a second contact surface that contacts the endplate of a second associated vertebral body;
wherein the implant is deployable, when positioned within a vertebral space between the first and second vertebral bodies, from a first non-expanded condition where the first contact surface has a first effective footprint area A1 to a second expanded condition where the first contact surface has a second effective footprint area A2, the ratio A2/A1 is at least 1.05; and,
wherein at least one of the first, second, third and fourth posts is laterally variable in response to a lateral load put on the implant by the first and second associated vertebral bodies after deployment of the implant.

28. The implant of claim 27 wherein at least two of the first, second, third and fourth posts are laterally variable in response to a lateral load put on the implant by the first and second associated vertebral bodies after deployment of the implant.

29. The implant of claim 27 wherein the post that is laterally variable is formed of a viscoelastic material.

* * * * *